United States Patent
Kanai et al.

(10) Patent No.: US 12,115,223 B2
(45) Date of Patent: Oct. 15, 2024

(54) CONJUGATE OF BIOTIN-MODIFIED DIMER AND PHTHALOCYANINE DYE

(71) Applicants: THE UNIVERSITY OF TOKYO, Tokyo (JP); SAVID THERAPEUTICS INC., Tokyo (JP)

(72) Inventors: Motomu Kanai, Tokyo (JP); Kenzo Yamatsugu, Tokyo (JP); Toshifumi Tatsumi, Tokyo (JP); Kazuki Takahashi, Tokyo (JP); Tatsuhiko Kodama, Tokyo (JP); Akira Sugiyama, Tokyo (JP); Takefumi Yamashita, Tokyo (JP); Masanobu Tsukagoshi, Tokyo (JP); Yuzo Toda, Tokyo (JP); Junji Nishigaki, Tokyo (JP)

(73) Assignees: THE UNIVERSITY OF TOKYO, Tokyo (JP); SAVID THERAPEUTICS INC., Tokyo (JP)

( * ) Notice: Subject to any disclaimer, the term of this patent is extended or adjusted under 35 U.S.C. 154(b) by 0 days.

(21) Appl. No.: 17/237,709

(22) Filed: Apr. 22, 2021

(65) Prior Publication Data
US 2023/0106135 A1  Apr. 6, 2023

(51) Int. Cl.
*A61K 47/64*  (2017.01)
*A61K 31/4188*  (2006.01)
*A61K 47/68*  (2017.01)

(52) U.S. Cl.
CPC .......... *A61K 47/64* (2017.08); *A61K 31/4188* (2013.01); *A61K 47/6803* (2017.08)

(58) Field of Classification Search
CPC . A61K 47/64; A61K 31/4188; A61K 47/6803
See application file for complete search history.

(56) References Cited

U.S. PATENT DOCUMENTS

| | | | |
|---|---|---|---|
| 5,824,799 A | 10/1998 | Buechler et al. | |
| 2017/0281789 A1 | 10/2017 | Basilion et al. | |

FOREIGN PATENT DOCUMENTS

| | | |
|---|---|---|
| CN | 103435639 A | 12/2013 |
| CN | 105669735 A | 6/2016 |
| CN | 106573054 A | 4/2017 |
| CN | 106866721 A | 6/2017 |
| CN | 107226839 A | 10/2017 |
| CN | 111166882 A | 5/2020 |
| JP | 10-508897 A | 9/1998 |
| JP | 6127045 | 5/2017 |
| JP | 2017-524659 | 8/2017 |
| JP | 2018-528268 A | 9/2018 |
| JP | 2021-054739 A | 4/2021 |
| WO | 96/29367 A1 | 9/1996 |
| WO | 2013/009475 | 1/2013 |
| WO | 2015/125820 | 8/2015 |
| WO | 2015/187677 | 12/2015 |
| WO | 2017-031367 A1 | 2/2017 |
| WO | 2020/060260 A1 | 3/2020 |
| WO | WO-2020138427 A1 * | 7/2020 ............ A61K 47/54 |
| WO | 2021/207691 A1 | 10/2021 |
| WO | 2022/182483 A1 | 9/2022 |

OTHER PUBLICATIONS

Li D, Wang XZ, Yang LF, Li SC, Hu QY, Li X, Zheng BY, Ke MR, Huang JD. ACS Appl Mater Interfaces. Oct. 9, 2019;11(40):36435-36443. doi: 10.1021/acsami.9b13861. Epub Sep. 26, 2019. PMID: 31525892. https://pubs.acs.org/doi/full/10.1021/acsami.9b13861 (Year: 2019).*

Machine Translation from google.com of WO2020138427, accessed Jan. 27, 2023 (Year: 2020).*

(Continued)

*Primary Examiner* — Adam Weidner
*Assistant Examiner* — Laura Ann Essex
(74) *Attorney, Agent, or Firm* — GREENBLUM & BERNSTEIN, P.L.C.

(57) ABSTRACT

[Object] It is an object of the present invention to provide a conjugate of a biotin-modified dimer and a phthalocyanine dye, which is used in photoimmunotherapy.
[Means for Solution] A compound represented by the following formula (1) or a salt thereof:

[Formula 1]

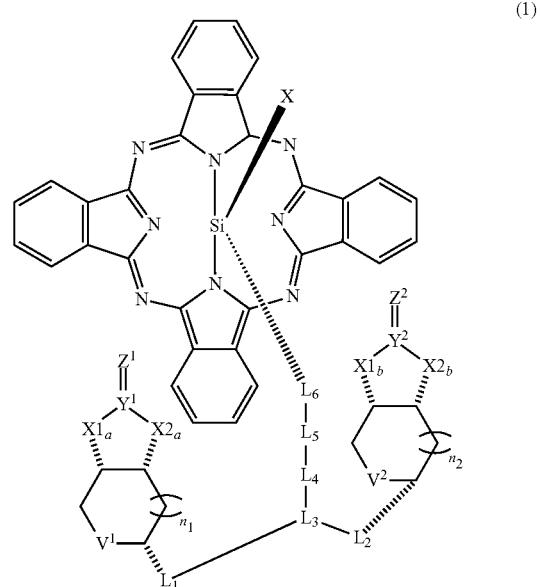

(1)

wherein X represents a substituent having a hydrophilic group, a cationic group or an amino group at the terminus thereof, or —OH, and other groups have the meanings as defined in the description.

20 Claims, 5 Drawing Sheets

Specification includes a Sequence Listing.

(56) References Cited

OTHER PUBLICATIONS

DeGuire SM, Earl DC, Du Y, Crews BA, Jacobs AT, Ustione A, Daniel C, Chong KM, Marnett LJ, Piston DW, Bachmann BO, Sulikowski GA. Angew Chem Int Ed Engl. Jan. 12, 2015;54(3):961-4. doi: 10.1002/anie.201408906. Epub Nov. 27, 2014. PMID: 25430909; PMCID: PMC4293314. (Year: 2015).*

Sato K, Ando K, Okuyama S, Moriguchi S, Ogura T, Totoki S, Hanaoka H, Nagaya T, Kokawa R, Takakura H, Nishimura M, Hasegawa Y, Choyke PL, Ogawa M, Kobayashi H. ACS Cent Sci. Nov. 28, 2018;4(11):1559-1569. doi: 10. 1021/acscentsci.8b00565. Epub Nov. 6, 2018. PMID: 30555909; PMCID: PMC6276043. (Year: 2018).*

Mitsunaga et al., "Cancer Cell-selective In Vivo Near Infrared Photoimmunotherapy Targeting Specific Membrane Molecules," *Nature Medicine*, vol. 17, No. 12, pp. 1685-1691, published online Nov. 6, 2011.

International Search Report and Written Opinion issued in PCT/JP2021/004100 dated Apr. 13, 2021, along with English translation thereof.

International Preliminary Report on Patentability issued in PCT/JP2021/004100 dated Jul. 28, 2022, along with English translation thereof.

Zheng et al., "Synthesis and Photodynamic activities of integrin-targeting silicon (IV) phthalocyanine-cRGD conjugates", European Journal of Medical Chemistry, 2018, vol. 155, pp. 24-33.

Galstyan et al., "Labeling and Selective Inactivation of Gram-Positive Bacteria Employing Bimodal Photoprobes with Duel Readouts", Chem. Eur. J., 2016, vol. 22, pp. 5243-5252.

Lin et al., "Combination of Optical and Electrical Loss Analyses for a Si-Phthalocyanine Dey-Sensitized Solar Cell" J. Phys. Chem. B, 2014, vol. 118, pp. 14027-14036.

U.S. Appl. No. 17/266,190, entitled "Conjugate of Biotin-Modified Dimer and Phthalocyanine Dye," filed Feb. 5, 2021; Applicant(s): The University of Tokyo, and Savid Therapeutics Inc.; Inventor(s): Motomu Kanai et al.

Office Action ("JP OA") that issued in corresponding Japanese Patent Application No. 2019-179281, dated Oct. 17, 2023, along with English Translation thereof.

JSMI Report, 2016, vol. 10, No. 1, pp. 43-45 (this reference was cited in the JP OA; Concise Statement of relevance may be found in the English Translation of the JP OA submitted herewith).

Takahashi et al., "23PO-am103", Abstract of the 139$^{th}$ Annual Meeting of the Pharmaceutical Society of Japan (Chiba), 2019, p. 210 (this reference was cited in the JP OA; Concise Statement of relevance may be found in the English Translation of the JP OA submitted herewith).

Pratesi et al., "Design and solid phase synthesis of new DOTA conjugated (+)-biotin dimers planned to develop molecular weight-tuned avidin oligomers", Organic & Biomolecular Chemistry, 2015, vol. 13, p. 3988-4001 (this reference was cited in the JP OA and is in English).

Office Action that issued in corresponding Japanese Patent Application No. 2019-179281, dated Mar. 26, 2024, along with English Translation.

Li et al., "A biotin receptor-targeted silicon(IV) phthalocyanine for in vivo tumor imaging and photodynamic therapy", Journal of Photochemistry & Photobiology, B:Biology, 190 (2019), pp. 1-7.

Office Action that issued in the related Chinese Patent Application No. 202180013061.X dated Dec. 15, 2023, along with its English machine translation.

Extend European Search Report that issued in corresponding European Patent Application No. 21750642.7, dated Jun. 11, 2024.

Office Action that issued in corresponding Chinese Patent Application No. 202180013061.X dated Aug. 24, 2024, along with its English translation.

\* cited by examiner

[Fig. 1]
Structural drawing of CEA-V2122
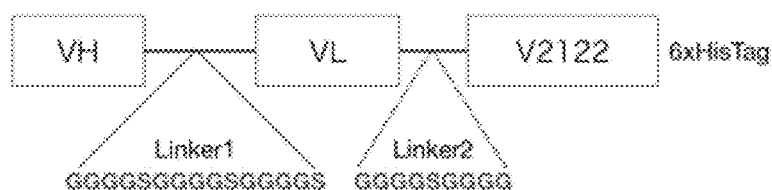
[Fig. 2]
Electrophoretic pattern of purified product
(1) E.coli secretion expression
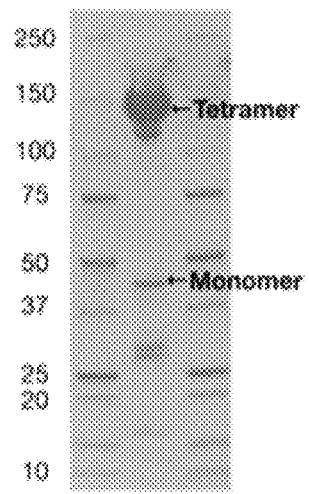

[Fig. 3]
Evaluation of binding performance of CEA-Cupid with antigen (CEACAM5)
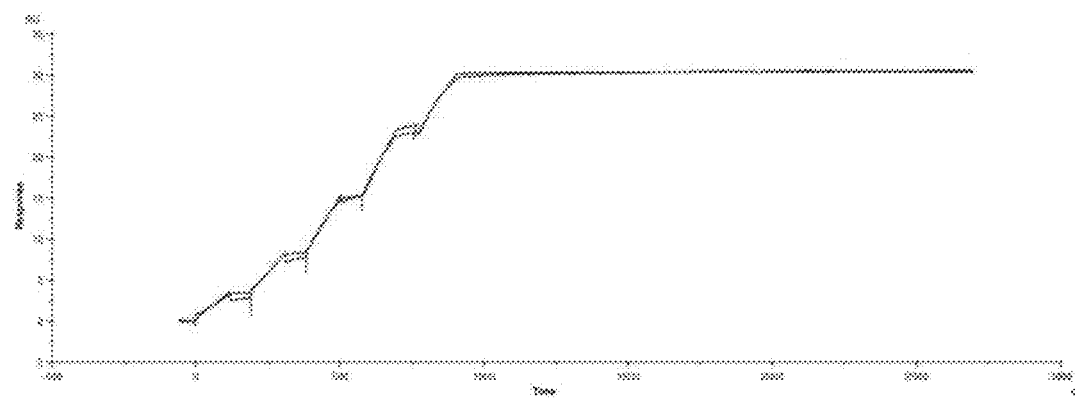
[Fig. 4]
Evaluation of binding performance of CEA-Cupid with modified biotin
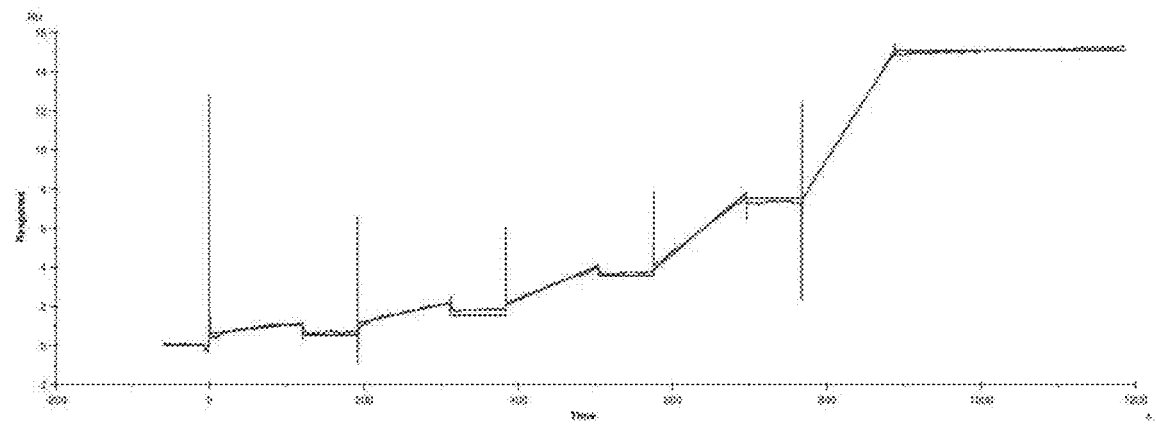

[Fig. 5]
Stained cell images obtained using FITC-labeled CEA-V2122
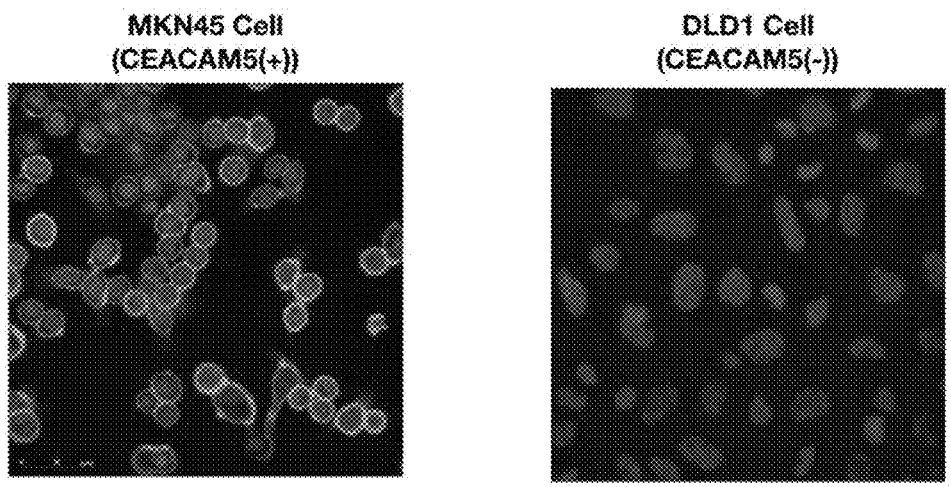
[Fig. 6]
Time-series data of stained MKN45 cell images obtained using FITC-labeled CEA-Cupid
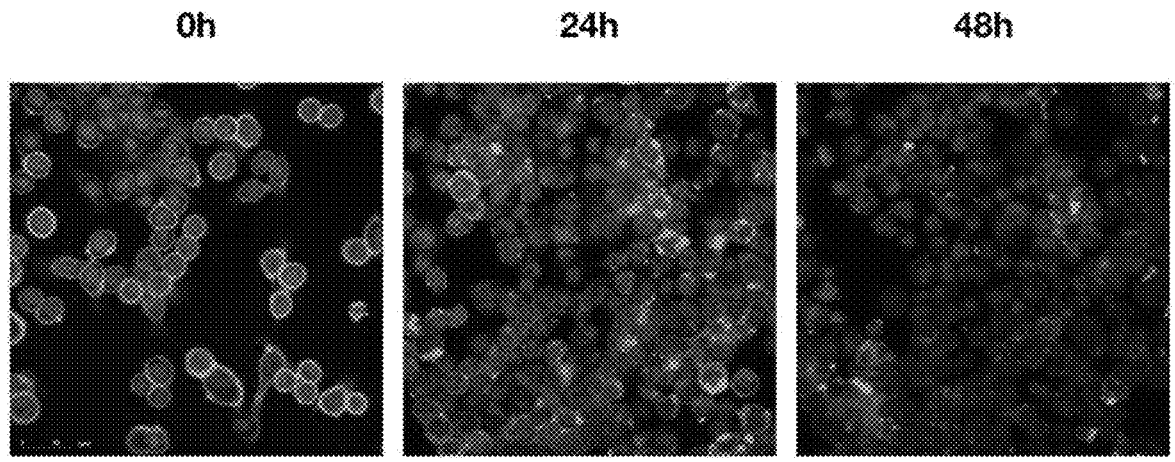

[Fig. 7]
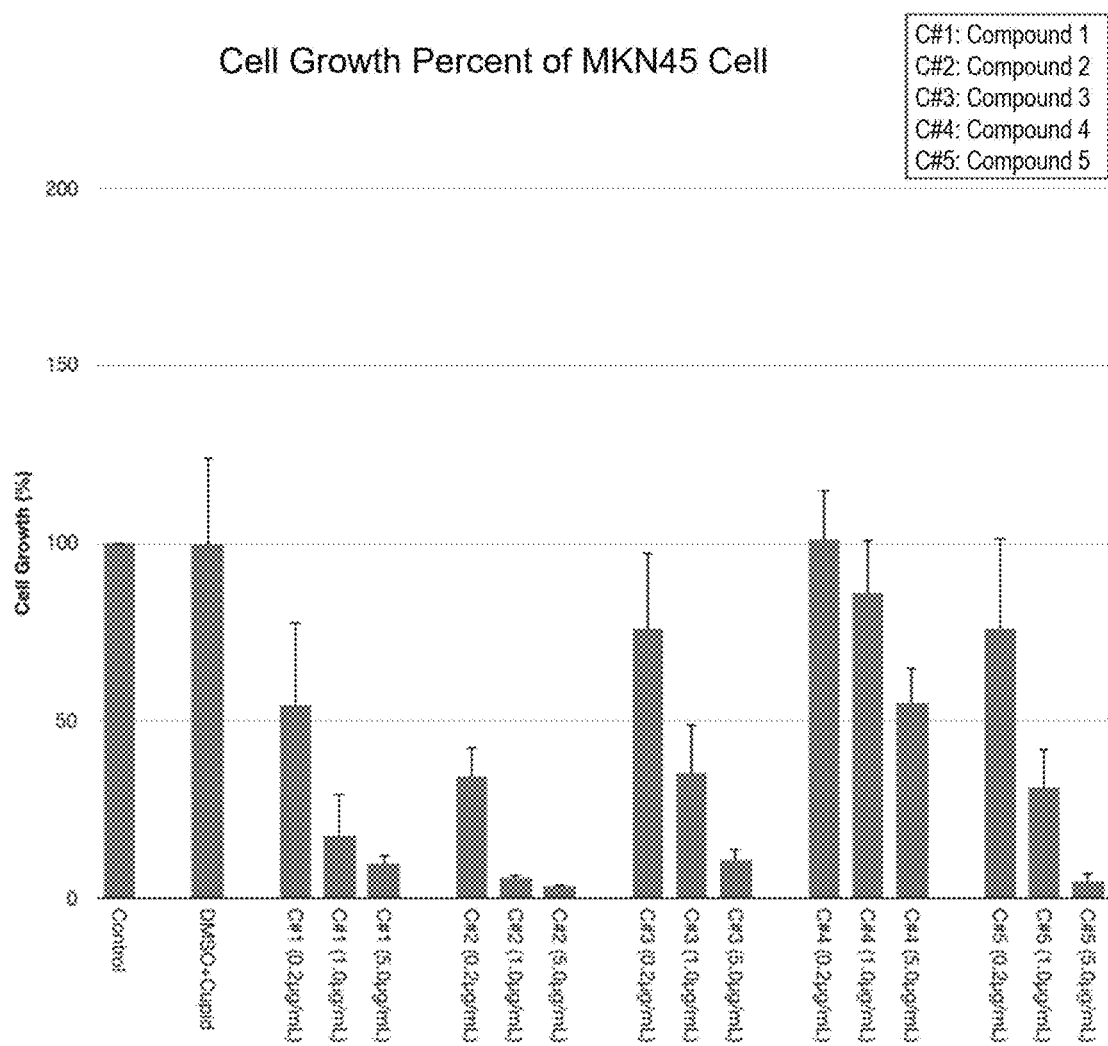

[Fig. 8]
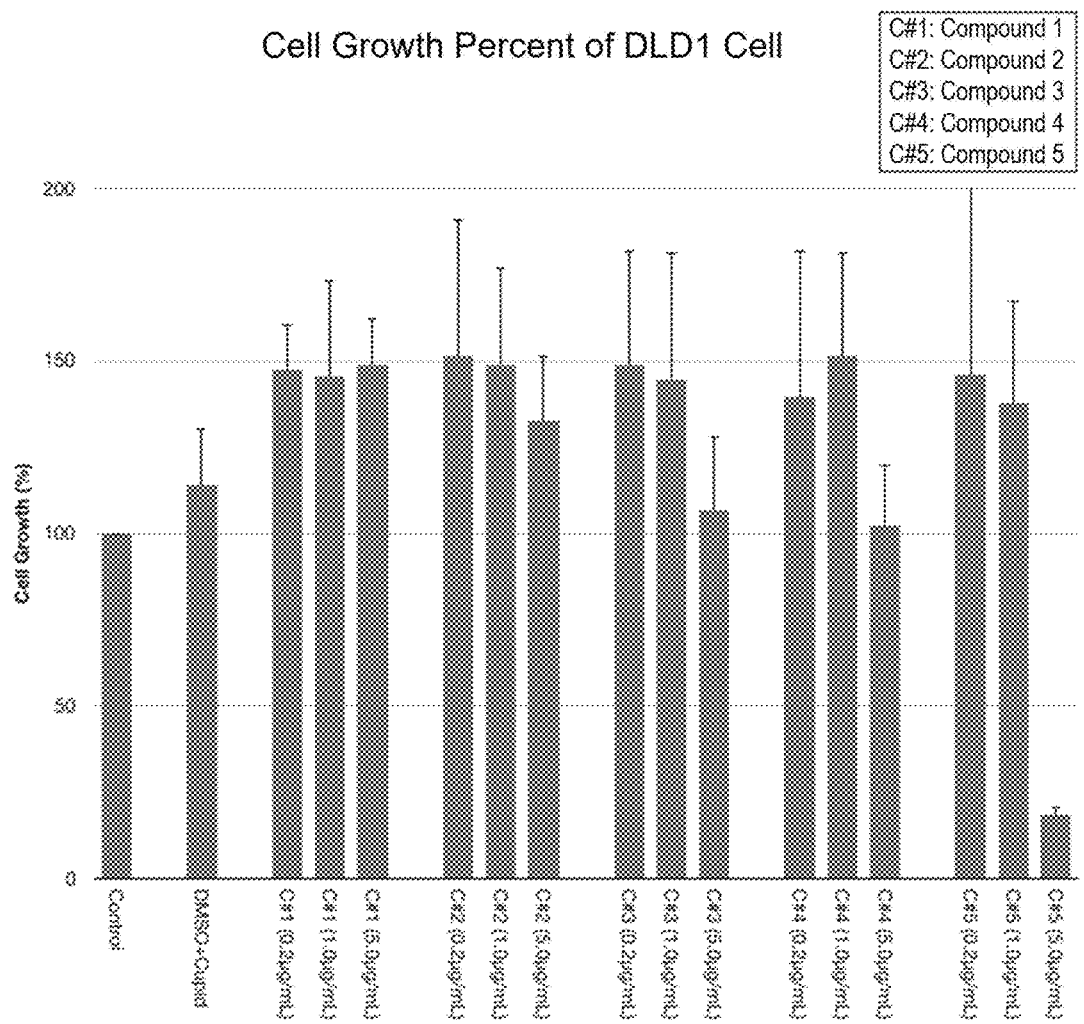

SEQUENCE LISTING

<160> NUMBER OF SEQ IDS NOS: 15

<210> SEQ ID NO 1
<211> LENGTH: 133
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 1

Ala Glu Ala Gly Ile Thr Gly Thr Trp Ser Asp Gln Leu Gly Asp Thr
1               5                   10                  15

Phe Ile Val Thr Ala Gly Ala Asp Gly Ala Leu Thr Gly Thr Tyr Glu
                20                  25                  30

Asn Ala Val Gly Ala Glu Ser Arg Tyr Val Leu Thr Gly Arg Tyr
            35                  40                  45

Asp Ser Ala Pro Ala Thr Asp Gly Ser Gly Thr Ala Leu Gly Trp Thr
    50                  55                  60

Val Ala Trp Lys Asn Asn Ser Lys Asn Ala His Ser Ala Thr Thr Trp
65                  70                  75                  80

Ser Gly Gln Tyr Val Gly Gly Ala Asp Ala Lys Ile Asn Thr Gln Trp
                85                  90                  95

Leu Leu Thr Ser Gly Thr Thr Asn Ala Asn Ala Trp Lys Ser Thr Leu
            100                 105                 110

Val Gly His Asp Thr Phe Thr Lys Val Lys Pro Ser Ala Ala Ser His
        115                 120                 125

His His His His His

130

<210> SEQ ID NO 2
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Arg Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ala Asn Thr Ala Tyr
65                  70                  75                  80

Leu Gly Leu Ser Ser Leu Arg Pro Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Glu Asn Val Leu Thr Gln Ser Pro Ser
    130                 135                 140

Ser Met Ser Val Ser Val Gly Asp Arg Val Asn Ile Ala Cys Ser Ala
145                 150                 155                 160

Ser Ser Ser Val Pro Tyr Met His Trp Leu Gln Gln Lys Pro Gly Lys
                165                 170                 175

Ser Pro Lys Leu Leu Ile Tyr Leu Thr Ser Asn Leu Ala Ser Gly Val
            180                 185                 190

Pro Ser Arg Phe Ser Gly Ser Gly Ser Gly Thr Asp Tyr Ser Leu Thr
        195                 200                 205

Ile Ser Ser Val Gln Pro Glu Asp Ala Ala Thr Tyr Tyr Cys Gln Gln
    210                 215                 220

Arg Ser Ser Tyr Pro Leu Thr Phe Gly Gly Gly Thr Lys Leu Glu Ile
225                 230                 235                 240

Lys

<210> SEQ ID NO 3
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Arg Leu Glu Trp Ile
        35                  40                  45

Gly Trp Ile Asp Pro Glu Asn Gly Asp Thr Glu Tyr Ala Pro Lys Phe
 50                  55                  60

Gln Gly Lys Ala Thr Phe Thr Thr Asp Thr Ser Ala Asn Thr Ala Tyr
 65                  70                  75                  80

Leu Gly Leu Ser Ser Leu Arg Pro Glu Asp Thr Ala Val Tyr Tyr Cys
                 85                  90                  95

Asn Glu Gly Thr Pro Thr Gly Pro Tyr Tyr Phe Asp Tyr Trp Gly Gln
             100                 105                 110

Gly Thr Leu Val Thr Val Ser Ser Gly Gly Gly Ser Gly Gly Gly
         115                 120                 125

Gly Ser Gly Gly Gly Ser Glu Asn Val Leu Thr Gln Ser Pro Ser
 130                 135                 140

Ser Met Ser Val Ser Val Gly Asp Arg Val Asn Ile Ala Cys Ser Ala
145                 150                 155                 160

Ser Ser Ser Val Pro Tyr Met His Trp Leu Gln Gln Lys Pro Gly Lys
                 165                 170                 175

Ser Pro Lys Leu Leu Ile Tyr Leu Thr Ser Asn Leu Ala Ser Gly Val
             180                 185                 190

Pro Ser Arg Phe Ser Gly Ser Gly Ser Gly Thr Asp Tyr Ser Leu Thr
         195                 200                 205

Ile Ser Ser Val Gln Pro Glu Asp Ala Ala Thr Tyr Tyr Cys Gln Gln
 210                 215                 220

Arg Ser Ser Tyr Pro Leu Thr Phe Gly Gly Gly Thr Lys Leu Glu Ile
225                 230                 235                 240

Lys Gly Gly Gly Gly Ser Gly Gly Gly Ala Glu Ala Gly Ile Thr
                 245                 250                 255

Gly Thr Trp Ser Asp Gln Leu Gly Asp Thr Phe Ile Val Thr Ala Gly
         260                 265                 270

Ala Asp Gly Ala Leu Thr Gly Thr Tyr Glu Asn Ala Val Gly Gly Ala
 275                 280                 285

Glu Ser Arg Tyr Val Leu Thr Gly Arg Tyr Asp Ser Ala Pro Ala Thr
290                 295                 300

Asp Gly Ser Gly Thr Ala Leu Gly Trp Thr Val Ala Trp Lys Asn Asn
305                 310                 315                 320

Ser Lys Asn Ala His Ser Ala Thr Thr Trp Ser Gly Gln Tyr Val Gly
                 325                 330                 335

Gly Ala Asp Ala Lys Ile Asn Thr Gln Trp Leu Leu Thr Ser Gly Thr
             340                 345                 350

Thr Asn Ala Asn Ala Trp Lys Ser Thr Leu Val Gly His Asp Thr Phe
         355                 360                 365

Thr Lys Val Lys Pro Ser Ala Ala Ser His His His His His His
 370                 375                 380

<210> SEQ ID NO 4
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Tyr Leu Leu Pro Thr Ala Ala Ala Gly Leu Leu Leu Leu Ala
 1               5                  10                  15

Ala Gln Pro Ala Met Ala Gln Val Lys Leu Glu Gln Ser Gly Ala Glu

```
            20                  25                  30
Val Val Lys Pro Gly Ala Ser Val Lys Leu Ser Cys Lys Ala Ser Gly
         35                  40                  45

Phe Asn Ile Lys Asp Ser Tyr Met His Trp Leu Arg Gln Gly Pro Gly
 50                  55                  60

Gln Arg Leu Glu Trp Ile Gly Trp Ile Asp Pro Glu Asn Gly Asp Thr
 65                  70                  75                  80

Glu Tyr Ala Pro Lys Phe Gln Gly Lys Ala Thr Phe Thr Thr Asp Thr
                 85                  90                  95

Ser Ala Asn Thr Ala Tyr Leu Gly Leu Ser Ser Leu Arg Pro Glu Asp
             100                 105                 110

Thr Ala Val Tyr Tyr Cys Asn Glu Gly Thr Pro Thr Gly Pro Tyr Tyr
         115                 120                 125

Phe Asp Tyr Trp Gly Gln Gly Thr Leu Val Thr Val Ser Ser Gly Gly
     130                 135                 140

Gly Gly Ser Gly Gly Gly Ser Gly Gly Gly Ser Glu Asn Val
145                 150                 155                 160

Leu Thr Gln Ser Pro Ser Ser Met Ser Val Ser Val Gly Asp Arg Val
                 165                 170                 175

Asn Ile Ala Cys Ser Ala Ser Ser Val Pro Tyr Met His Trp Leu
             180                 185                 190

Gln Gln Lys Pro Gly Lys Ser Pro Lys Leu Leu Ile Tyr Leu Thr Ser
         195                 200                 205

Asn Leu Ala Ser Gly Val Pro Ser Arg Phe Ser Gly Ser Gly Ser Gly
     210                 215                 220

Thr Asp Tyr Ser Leu Thr Ile Ser Ser Val Gln Pro Glu Asp Ala Ala
225                 230                 235                 240

Thr Tyr Tyr Cys Gln Gln Arg Ser Ser Tyr Pro Leu Thr Phe Gly Gly
                 245                 250                 255

Gly Thr Lys Leu Glu Ile Lys Gly Gly Gly Ser Gly Gly Gly Gly
             260                 265                 270

Ala Glu Ala Gly Ile Thr Gly Thr Trp Ser Asp Gln Leu Gly Asp Thr
         275                 280                 285

Phe Ile Val Thr Ala Gly Ala Asp Gly Ala Leu Thr Gly Thr Tyr Glu
     290                 295                 300

Asn Ala Val Gly Gly Ala Glu Ser Arg Tyr Val Leu Thr Gly Arg Tyr
305                 310                 315                 320

Asp Ser Ala Pro Ala Thr Asp Gly Ser Gly Thr Ala Leu Gly Trp Thr
                 325                 330                 335

Val Ala Trp Lys Asn Asn Ser Lys Asn Ala His Ser Ala Thr Thr Trp
             340                 345                 350

Ser Gly Gln Tyr Val Gly Gly Ala Asp Ala Lys Ile Asn Thr Gln Trp
         355                 360                 365

Leu Leu Thr Ser Gly Thr Thr Asn Ala Asn Ala Trp Lys Ser Thr Leu
     370                 375                 380

Val Gly His Asp Thr Phe Thr Lys Val Lys Pro Ser Ala Ala Ser His
385                 390                 395                 400

His His His His His
             405

<210> SEQ ID NO 5
<211> LENGTH: 1218
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 5

```
atgaaatatc tgctgccgac cgcagcagcg ggtctgctgc tgctggcagc acagcctgca      60
atggcacagg ttaaactgga acagagcggt gccgaagttg ttaaaccggg tgcaagcgtt     120
aaactgagct gtaaagcaag cggctttaac atcaaagata gctatatgca ttggctgcgt     180
cagggtccgg gtcagcgtct ggaatggatt ggttggattg atccggaaaa tggtgatacc     240
gaatatgcac cgaaatttca gggtaaagca acctttacca ccgataccag cgcaaatacc     300
gcatatctgg gtctgagcag cctgcgtccg gaagatacccg cagtgtatta ttgtaatgaa     360
ggcaccccga ccggtccgta ttatttcgat tattggggtc agggcaccct ggttaccgtt     420
agcagcggtg gtggtggtag tggtggcggt ggttcaggcg gtggcggtag cgaaaatgtt     480
ctgacccaga gcccgagcag catgagcgtt agcgttggtg atcgtgttaa tattgcatgt     540
agcgcaagca gcagcgttcc gtacatgcac tggctgcagc agaaaccggg taaaagcccg     600
aaactgctga tttatctgac cagcaatctg gcaagcggtg ttccgagccg ttttagcggt     660
agcggtagtg gcaccgatta tagcctgacc attagcagcg tgcagcctga agatgcagca     720
acctattatt gtcagcagcg tagcagttat ccgctgacct ttggtggtgg caccaaactg     780
gaaattaaag ggggtggtgg ctcaggtggc ggaggtgcag aagcaggtat taccggtaca     840
tggtcagatc agctgggtga tacctttatt gttaccgcag cgcagatggt gcactgacc      900
ggcacctatg aaaatgcagt tggtggtgca gaaagccgtt atgtgctgac cggtcgttat     960
gatagcgcac cggcaaccga tggtagcggc accgcactgg gttggaccgt tgcatggaaa    1020
aataacagca aaaatgcaca tagcgcaacc acctggtcag gtcagtatgt gggtggtgcc    1080
gatgccaaaa ttaacaccca gtggctgctg accagcggta caaccaatgc aaatgcctgg    1140
aaaagtaccc tggttggtca tgatacattc accaaagtta accgagcgc agcaagccat    1200
catcatcacc atcattaa                                                  1218
```

<210> SEQ ID NO 6
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Asp Lys Ile Ala Ile Val Asn Met Gly Ser Leu Phe Gln Gln Val
1               5                   10                  15

Ala Gln Lys Thr Gly Val Ser Asn Thr Leu Glu Asn Glu Phe Lys Gly
            20                  25                  30

Arg Ala Ser Glu Leu Gln Arg Met Glu Thr Asp Leu Gln Ala Lys Met
        35                  40                  45

Lys Lys Leu Gln Ser Met Lys Ala Gly Ser Asp Arg Thr Lys Leu Glu
    50                  55                  60

Lys Asp Val Met Ala Gln Arg Gln Thr Phe Ala Gln Lys Ala Gln Ala
65                  70                  75                  80

Phe Glu Gln Asp Arg Ala Arg Arg Ser Asn Glu Glu Arg Gly Lys Leu
                85                  90                  95

Val Thr Arg Ile Gln Thr Ala Val Lys Ser Val Ala Asn Ser Gln Asp
            100                 105                 110
```

-continued

```
Ile Asp Leu Val Val Asp Ala Asn Ala Val Ala Tyr Asn Ser Ser Asp
        115                 120                 125

Val Lys Asp Ile Thr Ala Asp Val Leu Lys Gln Val Lys
    130                 135                 140

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Gly Ser Gly Gly Gly Gly
1               5

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaggagatat acatatggat aaaattgcca ttgttaatat                          40

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttgagatctg ccatatgtta tttcacttgt ttcagaacg                           39

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agaaggagat ataccatgaa atatctgctg ccgac                               35

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 11
cgccgagctc gaattttaat gatggtgatg atgatg                                  36

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggtatatctc cttcttaaag ttaaac                                             26

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aattcgagct cggcgcgcct gcag                                               24

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His His His His His His
1               5

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Gly Ser Gly Gly Gly Gly Ser Gly Gly Gly Gly Ser
1               5                   10                  15
```

CONJUGATE OF BIOTIN-MODIFIED DIMER AND PHTHALOCYANINE DYE

SEQUENCE LISTING

The instant application contains a Sequence Listing which has been submitted electronically in ASCII format and is hereby incorporated by reference in its entirety. Said ASCII copy, created on Dec. 6, 2022, is named P63062_SL.txt and is 16,030 bytes in size.

TECHNICAL FIELD

The present invention relates to a conjugate of a biotin-modified dimer and a phthalocyanine dye and the use thereof.

BACKGROUND ART

Avidin and biotin, or streptavidin and biotin have an extremely high affinity between them ($Kd=10^{-15}$ to $10^{-14}$ M). This is one of the strongest interactions between two biomolecules. At present, the interaction between avidin/streptavidin and biotin has been widely applied in the field of biochemistry, molecular biology, or medicine. A drug delivery method and a pretargeting method, in which high binding ability between avidin/streptavidin and biotin is combined with an antibody molecule, have been devised. In connection with these studies, a mutant streptavidin with a reduced affinity for natural biotin and a biotin-modified dimer having a high affinity for the mutant streptavidin with a low affinity for natural biotin are reported in Patent Document 1.

On the other hand, photoimmunotherapy is a therapeutic method of using a photosensitizer and an irradiation light to destroy specific cells in a body. When a photosensitizer is exposed to a light with a specific wavelength, it generates cytotoxic reactive oxygen species capable of inducing apoptosis, necrosis, and/or autophagy to around cells. For example, Patent Document 2 discloses a method of killing cells, comprising: a step of allowing cells comprising a cell surface protein to come into contact with a therapeutically effective amount of one or more antibodies-IR700 molecules, wherein the antibodies specifically bind to the cell surface protein; a step of irradiating the cells with a light at a wavelength of 660 to 740 nm and at a dose of at least 1 $Jcm^{-2}$; and a step of allowing the cells to come into contact with one or more therapeutic agents at approximately 0 to 8 hours after the irradiation, thereby killing the cells. Patent Document 3 discloses a method of inducing cytotoxicity to a subject affected with a disease or a pathology, comprising: (a) administering to a subject, a therapeutically effective drug comprising a phthalocyanine dye such as IRDye (registered trademark) 700DX conjugated with a probe specifically binding to the cell of the subject; and (b) irradiating the cell with an appropriate excitation light in an amount effective for inducing cell death.

PRIOR ART DOCUMENTS

Patent Documents

[Patent Document 1] International Publication WO2015/125820
[Patent Document 2] Japanese Patent No. 6127045
[Patent Document 3] JP Patent Publication (Kohyo) No. 2017-524659 A

SUMMARY OF INVENTION

Object to be Solved by the Invention

It is an object of the present invention to provide a conjugate of a biotin-modified dimer and a phthalocyanine dye, which is used in photoimmunotherapy. It is another object of the present invention to provide a therapeutic kit, in which a combination of the above-described conjugate of a biotin-modified dimer and a phthalocyanine dye and a mutant streptavidin-molecular probe conjugate is used.

Means for Solving the Object

As a result of intensive studies directed towards achieving the above-described objects, the present inventor has found that the proliferation of cancer cells can be suppressed by photoimmunotherapy using a conjugate of a biotin-modified dimer and a phthalocyanine dye, thereby completing the present invention.

Specifically, according to the present invention, the following inventions are provided.

[1] A compound represented by the following formula (1) or a salt thereof:

(1)

[Formula 1]

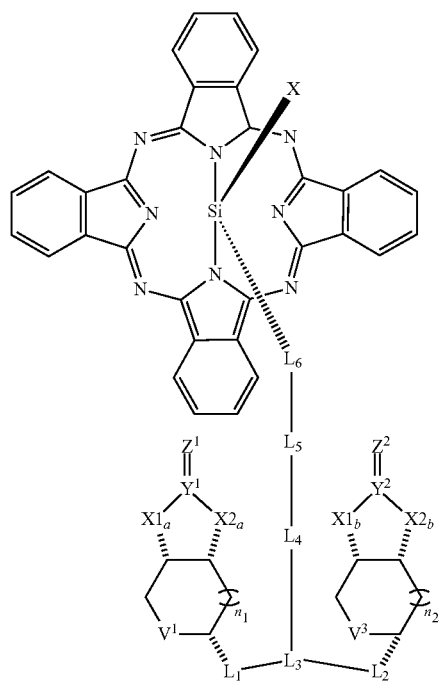

wherein
X represents a substituent having a hydrophilic group, a cationic group or an amino group at the terminus thereof, or —OH,
X1a, X1b, X2a and X2b each independently represent O or NH,
$Y^1$ and $Y^2$ each independently represent C or S,
$Z^1$ and $Z^2$ each independently represent O, S or NH,
$V^1$ and $V^2$ each independently represent S or $S^+$—$O^-$,
n1 and n2 each independently represent an integer of 0 or 1,
$L_1$ and $L_2$ each independently represent a divalent linking group,
$L_3$ represents a trivalent linking group,
$L_4$, $L_5$, and $L_6$ each independently represent a divalent linking group.

[2] The compound according to [1] or a salt thereof, which is represented by the following formula (2):

[Formula 2]

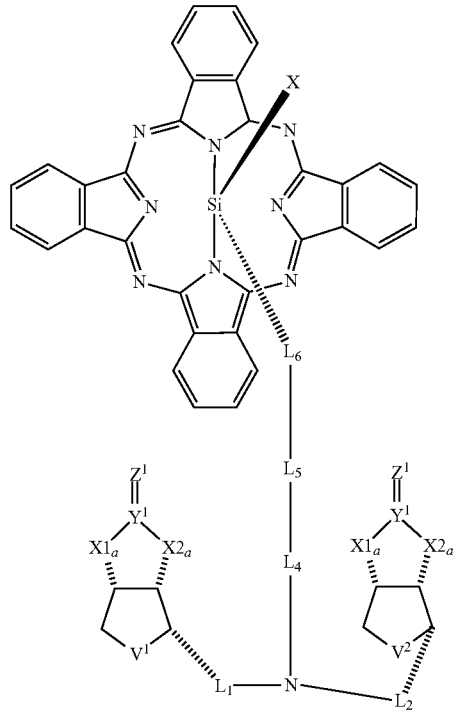

(2)

wherein each symbol is as defined in claim 1.

[3] The conjugate according to [1] or [2], wherein X1a, X1b, X2a and X2b represent NH; $Y^1$ and $Y^2$ represent C; $Z^1$ and $Z^2$ represent NH; and $V^1$ and $V^2$ represent S.

[4] The conjugate according to any one of [1] to [3], wherein $L_1$ and $L_2$ each independently represent a divalent linking group consisting of a combination of groups selected from —CONH—, —NHCO—, —COO—, —OCO—, —CO—, —O—, and an alkylene group containing 1 to 10 carbon atoms.

[5] The conjugate according to any one of [1] to [4], wherein $L_4$ represents a group consisting of a combination of groups selected from —CONH—, —NHCO—, —COO—, —OCO—, —CO—, —O—, —NH—, and an alkylene group containing 1 to 10 carbon atoms.

[6] The conjugate according to any one of [1] to [5], wherein $L_5$ represents

[Formula 3]

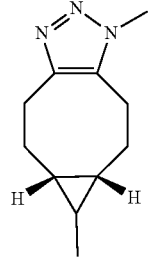

a triazole group, —S—, —CONH—, —NHCO—, —COO—, —OCO—, —CO—, —O—, —NH—, an alkylene group containing 1 to 10 carbon atoms, or a group consisting of a combination of these groups.

[7] The conjugate according to any one of [1] to [6], wherein $L_6$ represents —Si($R^1$)($R^2$)—O—, —CONH—, —NHCO—, —COO—, —OCO—, —CO—, —O—, —NH—, an alkylene group containing 1 to 10 carbon atoms, or a group consisting of a combination of these groups.

[8] The conjugate according to any one of [1] to [7], wherein the substituent having a hydrophilic group, a cationic group or an amino group at the terminus thereof, which is represented by X, is any one of the following:

[Formula 4]

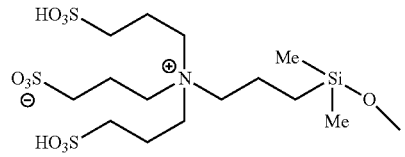

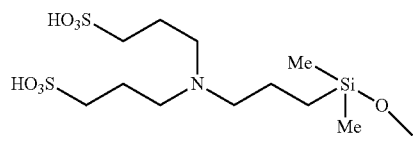

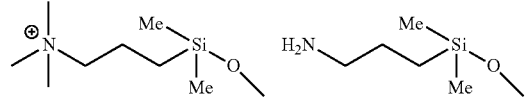

[9] A compound of any one of the following:
[Formula 5]
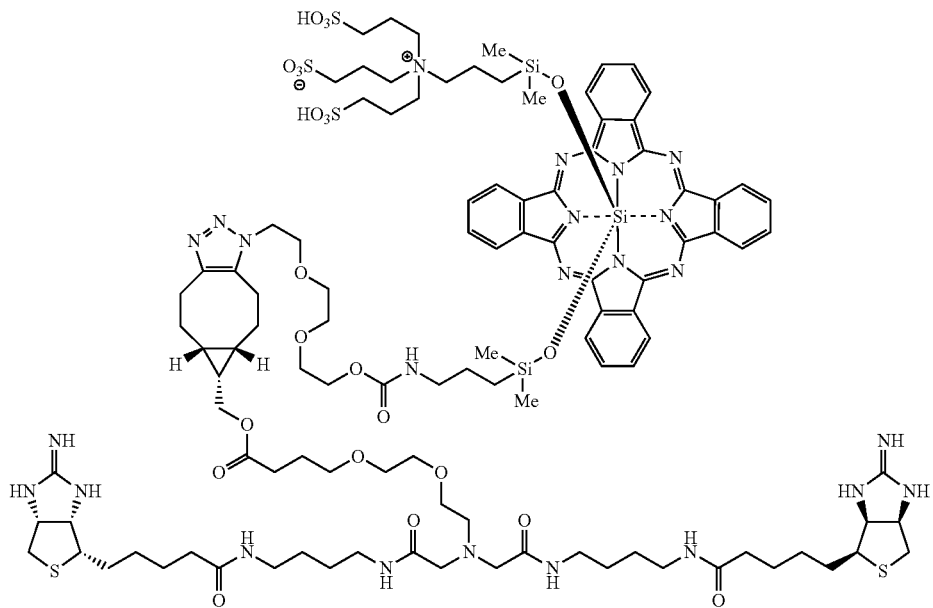
10
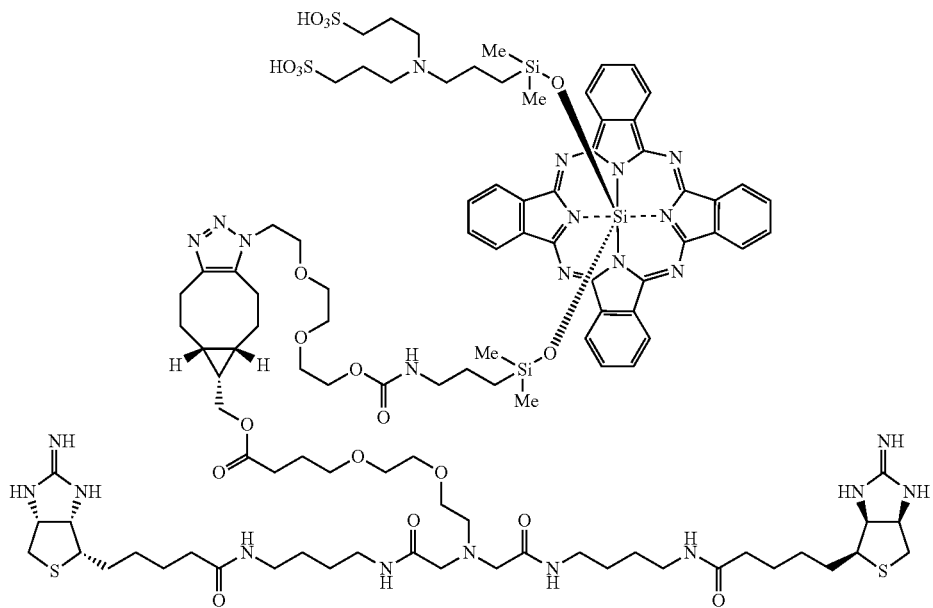
11

-continued
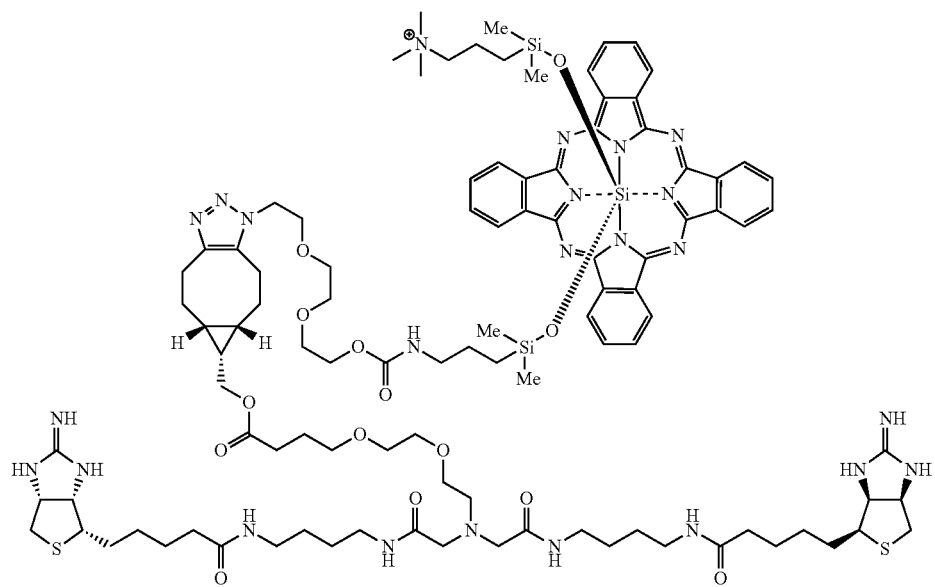
13
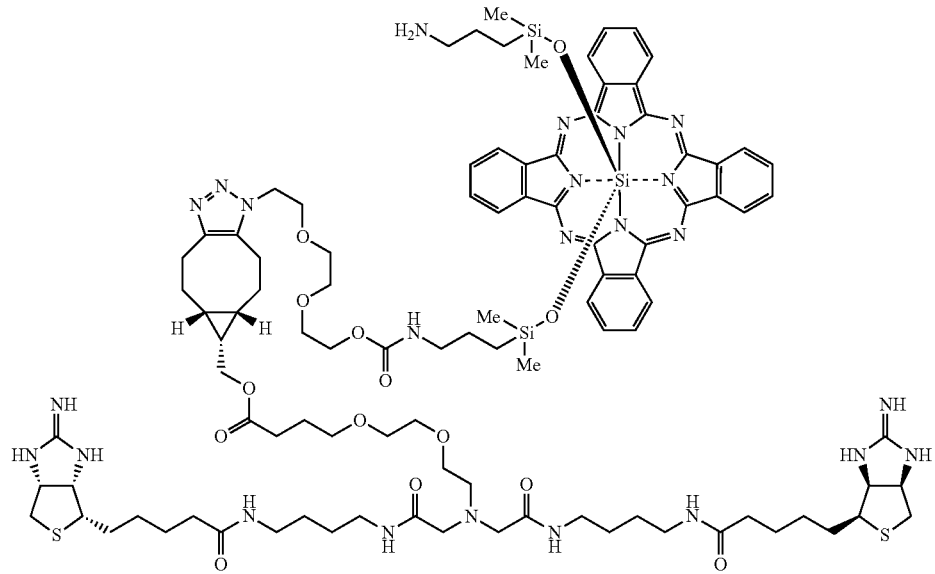
14

-continued

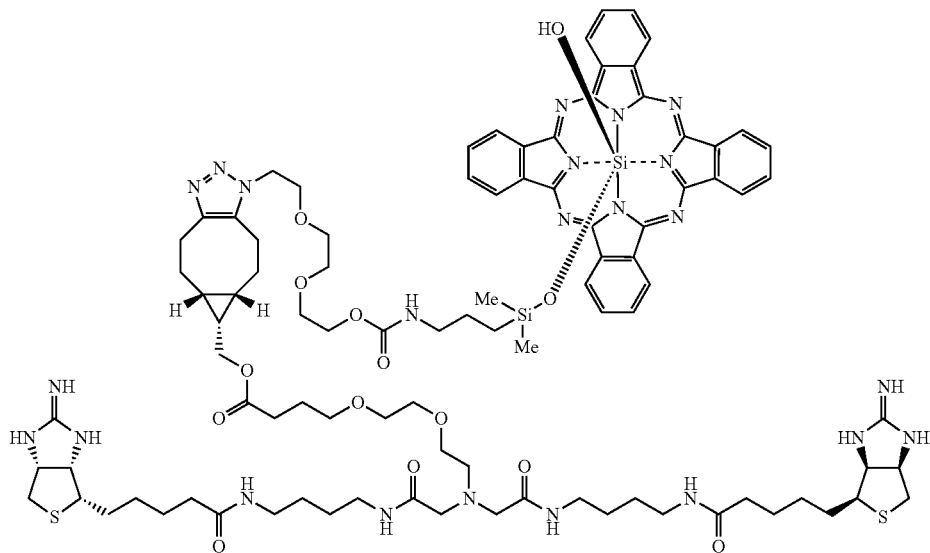

[10] A therapeutic agent comprising the conjugate according to any one of [1] to [9].

[11] A therapeutic kit comprising: (1) the conjugate according to any one of [1] to [9]; and (b) a conjugate of a mutant streptavidin comprising the amino acid sequence as set forth in SEQ ID NO: 1 (provided that a part of or the entire histidine tag at the C-terminus may be deleted) and a molecular probe.

[12] The therapeutic kit according to [11], wherein the molecular probe is an anti-EREG antibody, an anti-CEA antibody, or an anti-HER2 antibody.

Advantageous Effects of Invention

The proliferation of cancer cells can be suppressed by photoimmunotherapy using the conjugate of a biotin-modified dimer and a phthalocyanine dye according to the present invention

BRIEF DESCRIPTION OF DRAWINGS

FIG. 1 shows a structural drawing of CEA-V2122. Figure discloses SEQ ID NOS 14, 15, and 7, respectively in order of appearance.

FIG. 2 shows an electrophoretic pattern of a purified product.

FIG. 3 shows evaluation of the binding performance of CEA-Cupid with an antigen (CEACAM5).

FIG. 4 shows evaluation of the binding ability of CEA-Cupid with a modified biotin.

FIG. 5 shows stained cell images obtained using FITC-labeled CEA-V2122.

FIG. 6 shows time-series data of stained cell images (MKN45 cells) obtained using FITC-labeled CEA-Cupid.

FIG. 7 shows the results of an in vitro cytotoxicity test, in which CEA-V2122 and a photoactivatable compound-labeled modified biotin.

FIG. 8 shows the results of an in vitro cytotoxicity test, in which CEA-V2122 and a photoactivatable compound-labeled modified biotin.

EMBODIMENT OF CARRYING OUT THE INVENTION

Hereinafter, the present invention will be described in more detail.

(1) Biotin-Modified Dimer

The present invention relates to a conjugate of a biotin-modified dimer and a phthalocyanine dye, and the conjugate is a compound represented by the following formula (1) or a salt thereof, and is preferably a compound represented by the following formula (2) or a salt thereof.

[Formula 6]

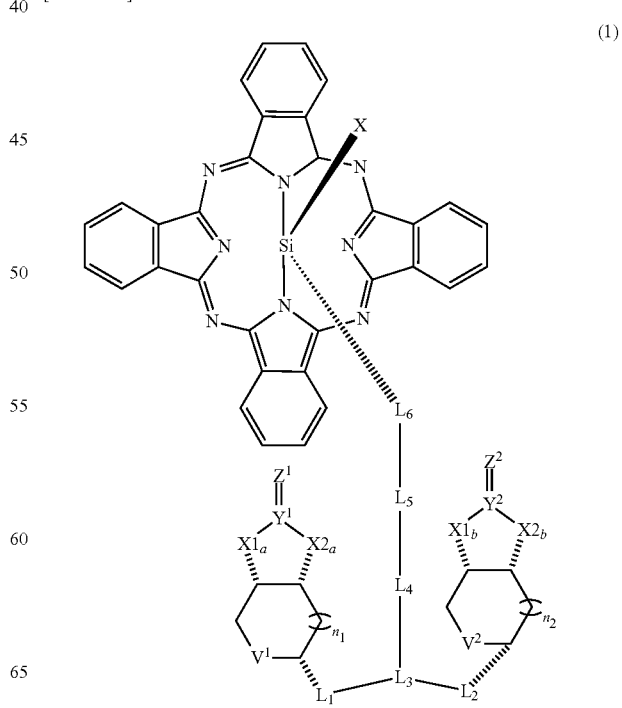

(1)

[Formula 7]

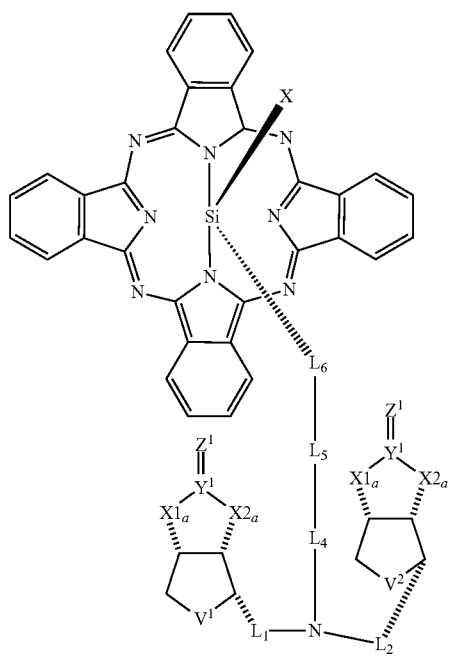

(2)

The biotin-modified dimer moiety is a compound represented by the following formula (11) or a salt thereof, and is preferably a compound represented by the following formula (12) or a salt thereof. As such a biotin-modified dimer, the compound described in International Publication WO2015/125820 can be used.

[Formula 8]

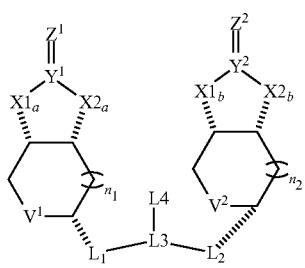

(11)

[Formula 9]

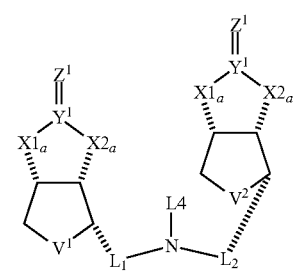

(12)

wherein, in the above formulae,
X1a, X1b, X2a and X2b each independently represent O or NH,
Y¹ and Y² each independently represent C or S,
Z¹ and Z² each independently represent O, S or NH,
V¹ and V² each independently represent S or S⁺—O⁻,
n1 and n2 each independently represent an integer of 0 or 1,
$L_1$ and $L_2$ each independently represent a divalent linking group,
$L_3$ represents a trivalent linking group, and
$L_4$ represents a divalent linking group.

In the above formulae, the portions represented by the following structures:

[Formula 10]

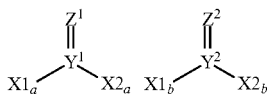

are preferably any one of the following portions, but are not limited thereto:

[Formula 11]

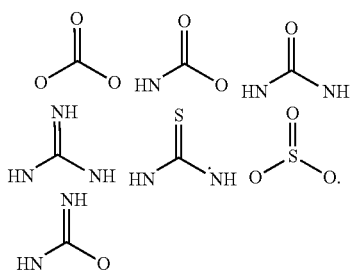

X1a, X1b, X2a and X2b preferably represent NH; Y¹ and Y² preferably represent C; Z¹ and Z² preferably represent NH; and V¹ and V² preferably represent S.

$L_1$ and $L_2$ each independently represent a divalent linking group consisting of a combination of groups selected from —CONH—, —NHCO—, —COO—, —OCO—, —CO—, —O—, and an alkylene group containing 1 to 10 carbon atoms.

Preferably, $L_1$ and $L_2$ each independently represent a divalent linking group consisting of a combination of groups selected from —CONH—, —NHCO—, —O—, and an alkylene group containing 1 to 10 carbon atoms.

Preferably, $L_1$ and $L_2$ each independently represent a divalent linking group consisting of a combination of groups selected from —CONH—, —NHCO—, and an alkylene group containing 1 to 10 carbon atoms.

$L_3$ represents a trivalent linking group, and is preferably the following:

[Formula 12]

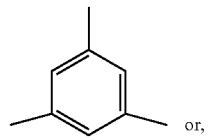 or,

[Formula 13]

(which is a benzene-derived trivalent linking group or a nitrogen atom).

$L_4$ is preferably a group consisting of a combination of groups selected from —CONH—, —NHCO—, —COO—, —OCO—, —CO—, —O—, —NH—, and an alkylene group containing 1 to 10 carbon atoms.

$L_5$ is preferably

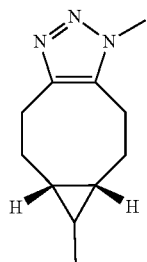

[Formula 14]

a triazole group, —S—, —CONH—, —NHCO—, —COO—, —OCO—, —CO—, —O—, —NH—, an alkylene group containing 1 to 10 carbon atoms, or a group consisting of a combination of these groups.

$L_6$ is preferably —Si($R^1$)($R^2$)—O—, —CONH—, —NHCO—, —COO—, —CO—, —CO—, —O—, —NH—, an alkylene group containing 1 to 10 carbon atoms, or a group consisting of a combination of these groups.

The substituent having a hydrophilic group, a cationic group or an amino group at the terminus thereof, which is represented by X, is preferably any one of the following:

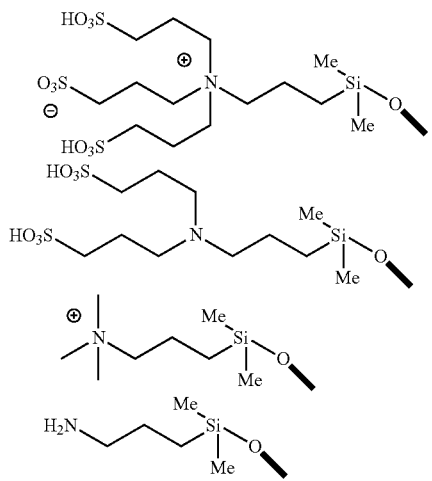

[Formula 15]

(2) Phthalocyanine Dye

The phthalocyanine dye is preferably a silicon phthalocyanine dye. Specific examples of the phthalocyanine dye, such as IRDye (registered trademark) 700DX, are described in, for example, U.S. Pat. No. 7,005,518. As a phthalocyanine dye, a commercially available product, such as IRDye (registered trademark) 700DX, can be used.

As such a phthalocyanine dye, a dye represented by the following formula can be used. The asterisk represents a binding site with a linking group for linking a biotin-modified dimer.

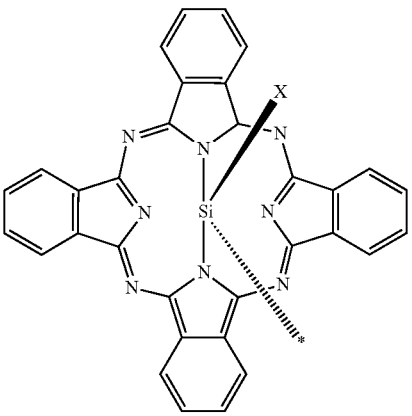

[Formula 16]

The compound of the present invention can be synthesized in accordance with the methods described in Production Examples 1 to 5 of the following Examples.

(3) Therapeutic Kit Using Conjugate of Biotin-Modified Dimer and Phthalocyanine Dye According to the present invention, provided is a therapeutic kit, in which the conjugate of a biotin-modified dimer and a phthalocyanine dye of the present invention is combined with a mutant streptavidin-molecular probe conjugate.

As mutant streptavidins used herein, those described in International Publication WO2014/129446 and International Publication WO2015/125820 can be used. Particularly preferably, the mutant streptavidin LISA314-V2122 described in Example 3 of International Publication WO2015/125820 (SEQ ID NO: 4 of International Publication WO2015/125820) (SEQ ID NO: 1 of the description of the present application) can be used.

Examples of the molecular probe used herein may include an antibody, a peptide, a nucleic acid, and an aptamer. Specifically, an antibody, a peptide, a nucleic acid, an aptamer, etc., which target the following antigens specifically expressed in cancer, can be used:

Epiregulin (EREG), ROBO 1, 2, 3, and 4, 1-40-β-amyloid, 4-1BB, SAC, 5T4, ACVR2B, adenocarcinoma antigen, α-fetoprotein, angiopoetin 2, anthrax toxin, AOC3 (VAP-1), B-lymphoma cells, B7-H3, BAFF, amyloid, C242 antigen, C5, CA-125, carbonic anhydrase 9 (CA-IX), cardiac myosin, CCL11 (eotaxin-1), CCR4, CCR5, CD11, CD18, CD125, CD140a, CD147 (basigin), CD147 (basigin), CD15, CD152, CD154 (CD40L), CD154, CD19, CD2, CD20, CD200, CD22, CD221, CD23 (Ty receptor), CD25 (IL-2 receptor α chain), CD28, CD3, CD30 (TNFRSF8), CD33, CD37, CD38 (cyclic ADP ribose hydrolase), CD4, CD40, CD41 (integrin α-IIb), CD44 v6, CD5, CD51, CD52, CD56, CD6, CD70, CD74, CD79B, CD80, CEA, CFD, ch4D5, CLDN18.2, *Clostridium difficile*, clumping factor A, CSF2, CTLA-4, cytomegalovirus, cytomegalovirus glycoprotein B, DLL4, DR5, *E. coli* Shiga toxin type 1, *E. coli* Shiga toxin type 2, EGFL7, EGFR, endotoxin, EpCAM, episialin, ERBB3, *Escherichia coli*, F protein of respiratory syncytial virus, FAP, fibrin II β chain, fibronectin extra domain-B, folate receptor 1, Frizzled receptor, GD2, GD3 ganglioside, GMCSF receptor α chain, GPNMB, hepatitis B surface antigen, hepatitis B virus, HER1, HER2/neu, HER3, HGF, HIV-1, HLA-DRβ, HNGF, Hsp90, human β amyloid, human scatter factor receptor kinase, human TNF, ICAM-1 (CD54), IFN-α, IFN-γ, IgE, IgE Fc region, IGF-1 receptor, IGF-I, IgG4, IGHE, IL-1β, IL-12, IL-13, IL-17, IL-17A, IL-22, IL-23, IL-4, IL-5, IL-6, IL-6 receptor, IL-9, ILGF2, influenza A hemagglutinin, insulin-like growth factor I receptor, integrin α4, integrin α4β7, integrin α5β1, integrin α7β7, integrin αIIbβ3, integrin αvβ3, integrin γ induced protein, interferon receptor, interferon α/β receptor, ITGA2, ITGB2 (CD18), KIR2D, L-selectin (CD62L), Lewis-Y antigen, LFA-1 (CD11a), lipoteichoic acid, LOXL2, LTA, MCP-1, mesothelin, MS4A1, MUC1, mucin CanAg, myostatin, N-glycolylneuraminic acid, NARP-1, NCA-90 (granulocyte antigen), NGF, NOGO-A, NRP1, *Oryctolagus cuniculus*, OX-40, oxLDL, PCSK9, PD-1, PDCD1, PDGF-R α, phosphatidylserine, prostate cancer cells, *Pseudomonas aeruginosa*, Rabies virus glycoprotein, RANKL, respiratory syncytial virus, RHD, Rh (Rhesus) factor, RON, RTN4, sclerostin, SDC1, selectin P, SLAMF7, SOST, sphingosine-1-phosphate, TAG-72, TEM1, tenascin C, TFPI, TGFβ1, TGFβ2, TGF-β, TNF-α, TRAIL-R1, TRAIL-R2, tumor antigen CTAA16.88, MUC1 tumor-specific glycosylation, TWEAK receptor, TYRP1 (glycoprotein 75), VEGF-A, VEGFR-1, VEGFR2, vimentin, and VWF.

Among the above-described antigens, epiregulin (EREG), CEA, and HER2 are preferable.

A fusion body of a molecular probe such as a tumor antigen-specific antibody molecule and a mutant streptavidin is prepared, and the prepared fusion body is then administered to a patient, so that the mutant streptavidin is allowed to be accumulated specifically in cancer cells. Subsequently, a conjugate of a biotin-modified dimer and a phthalocyanine dye having an affinity for the above-described mutant streptavidin is administered to the patient, so that the phthalocyanine dye can be accumulated exactly in the cancer cells.

Otherwise, in the present invention, a complex is prepared by binding a conjugate of a molecular probe such as a tumor antigen-specific antibody molecule and a mutant streptavidin with a conjugate of a biotin-modified dimer and a phthalocyanine dye, and the thus prepared complex can be administered to a patient.

Various types of molecules can be used as antibodies that are to be bound to the mutant streptavidin. Either a polyclonal antibody or a monoclonal antibody may be used. The subclass of the antibody is not particularly limited. Preferably, IgG, and particularly preferably, IgG$_1$ is used. Furthermore, the term "antibody" includes all of modified antibodies and antibody fragments. Examples of such an antibody include, but are not limited to: a humanized antibody; a human type antibody; a human antibody; antibodies from various types of animals such as a mouse, a rabbit, a rat, a guinea pig and a monkey; a chimeric antibody between a human antibody and an antibody from a different type of animal; diabody; scFv; Fd; Fab; Fab'; and F(ab')'$_2$.

The conjugate of the mutant streptavidin and the antibody can be obtained by applying a method known to persons skilled in the art. For example, such a conjugate can be obtained by a chemical bond method (U.S. Pat. No. 5,608, 060). Alternatively, DNA encoding the mutant streptavidin is ligated to DNA encoding an antibody, and using an expression vector or the like, the ligated DNA is then expressed in a host cell, so that such a conjugate can be obtained in the form of a fusion protein. The DNA encoding the mutant streptavidin may be ligated to the DNA encoding an antibody via DNA encoding a suitable peptide, called a linker. The mutant streptavidin-molecular probe conjugate is desirably produced, while keeping the specific binding force between an antibody and a target molecule.

(4) Photoimmunotherapy

The conjugate of a biotin-modified dimer and a phthalocyanine dye according to the present invention is administered to a subject, and the cells are then irradiated with an excitation light in an amount effective for suppression of cell proliferation or induction of cell death, so that the cell proliferation can be suppressed or the cell death can be induced, and thereby the subject can be treated.

Preferably a complex of the conjugate of a biotin-modified dimer and a phthalocyanine dye according to the present invention and a mutant streptavidin-molecular probe conjugate is administered to a subject, and the cells are then irradiated with an excitation light in an amount effective for suppression of cell proliferation or induction of cell death, so that the cell proliferation can be suppressed or the cell death can be induced, and thereby the subject can be treated.

The subject includes humans and non-human animals. Examples of the subject may include humans and experimental animals such as mice. The subject is preferably affected with a disease regarding which suppression of cell proliferation or induction of cell death is desired. For example, the subject is affected with cancer or solid tumor.

Examples of the "cancer" may include carcinoma, lymphoma, blastoma, sarcoma, and leukemia or malignant lymphoma. Specific examples of the cancer may include squamous cell carcinoma (e.g., epithelial squamous cell carcinoma), lung cancer including small cell lung cancer, non-small cell lung cancer ("NSCLC"), pulmonary adenocarcinoma and pulmonary squamous cell carcinoma, peritoneal cancer, hepatocarcinoma, corpus ventriculi or stomach cancer, including digestive cancer, pancreatic cancer, glioblastoma, cervical cancer, ovarian cancer, liver cancer, bladder cancer, hepatocellular cancer, breast cancer, colon cancer, rectal cancer, colorectal cancer, endometrial membrane cancer or endometrial carcinoma, salivary gland carcinoma, kidney or renal region cancer, prostate cancer, vulvar cancer, thyroid cancer, hepatocellular carcinoma, anal carcinoma, penile carcinoma, and head and neck cancer.

The solid tumor means a benign or malignant, abnormal cell mass that generally does not contain a capsule. Examples of the solid tumor may include glioma, astrocytoma, medulloblastoma, craniopharyngioma, ependymoma, pineal gland tumor, hemangioblastoma, acoustic neuroma, oligodendrocyte, meningioma, melanoma, neuroblastoma, and retinoblastoma.

In the photoimmunotherapy, the "conjugate of a biotin-modified dimer and a phthalocyanine dye" or the "complex of the conjugate of a biotin-modified dimer and a phthalocyanine dye and a mutant streptavidin-molecular probe conjugate" is administered to a subject, and thereafter, the subject is irradiated with a light, so that the subject can be treated.

Examples of the administration method to the subject may include, but are not limited to, a local route, an injection (a subcutaneous injection, an intramuscular injection, an intradermal injection, an intraperitoneal injection, an intratumoral injection, an intravenous injection, etc.), an oral route, an ocular route, a sublingual route, a rectal route, a percutaneous route, an intranasal route, a vaginal route, and an inhalation route.

The "conjugate of a biotin-modified dimer and a phthalocyanine dye" or the "complex of the conjugate of a biotin-modified dimer and a phthalocyanine dye and a mutant streptavidin-molecular probe conjugate" is preferably administered in a therapeutically effective amount. The therapeutically effective amount per 60 kg is at least 0.5 mg (mg/60 kg), at least 5 mg/60 kg, at least 10 mg/60 kg, at least 20 mg/60 kg, at least 30 mg/60 kg, or at least 50 mg/60 kg.

For example, when it is intravenously administered, the applied dose is 1 mg/60 kg, 2 mg/60 kg, 5 mg/60 kg, 20 mg/60 kg, or 50 mg/60 kg, and it is, for example, 0.5 to 50 mg/60 kg. In another example, the therapeutically effective amount is at least 100 μg/kg, at least 500 μg/kg or at least 500 μg/kg, and it is, for example, at least 10 μ/kg. For example, when it is intratumorally or intraperitoneally administered, the dose is 100 μg/kg, 250 μg/kg, approximately 500 μg/kg, 750 μg/kg, or 1000 μg/kg, and it is, for example, 10 μg/kg to 1000 μg/kg. In one example, when it is administered in the form of a solution for local administration, the therapeutically effective amount is 10 μg/ml, 20 μg/ml, 30 μg/ml, 40 μg/ml, 50 μg/ml, 60 μg/ml, 70 μg/ml, 80 μg/ml, 90 μg/ml, 100 μg/ml or the like, or it is 20 μg/ml to 100 μg/ml, or it is at least 500 μg/ml, or at least 1 μg/ml.

The above-described dose can be administered once or divided doses over several administrations (2, 3, or 4 times, etc.), or as a single preparation.

The "conjugate of a biotin-modified dimer and a phthalocyanine dye" or the "complex of the conjugate of a biotin-modified dimer and a phthalocyanine dye and a mutant streptavidin-molecular probe conjugate" can be administered alone, or can also be administered in the presence of a pharmaceutically acceptable carrier, or can also be administered in the presence of other therapeutic agents (other anticancer agents, etc.).

The "conjugate of a biotin-modified dimer and a phthalocyanine dye" or the "complex of the conjugate of a biotin-modified dimer and a phthalocyanine dye and a mutant streptavidin-molecular probe conjugate" can bind to target cells or target tissues, such as circulating tumor cells or solid tumor cells. Thereafter, the target cells or tissues are irradiated with a light, so that the above-described conjugate or complex can absorb the light and can damage or destroy the target cells or tissues.

In the photoimmunotherapy, the wavelength of the irradiation light is preferably 660 to 740 nm, and the irradiation light has a wavelength of, for example, 660 nm, 670 nm, 680 nm, 690 nm, 700 nm, 710 nm, 720 nm, 730 nm, or 740 nm. Light irradiation may be carried out using a device equipped with a near infrared (NIR) light emitting diode.

The light irradiation amount is at least 1 J/cm$^2$, for example, at least 4 J/cm$^2$, at least 10 J/cm$^2$, at least 15 J/cm$^2$, at least 20 J/cm$^2$, at least 50 J/cm$^2$, or at least 100 J/cm$^2$. It is, for example, 1 to 500 J/cm$^2$. Light irradiation may be carried out several times (e.g., 2, 3, 4, 5, 6, 7, 8, 9, or 10 times).

The entire contents disclosed in Japanese Patent Application No. 2019-179281 filed on Sep. 30, 2019, are incorporated herein by reference in their entireties.

The present invention will be more specifically described in the following examples. However, these examples are not intended to limit the scope of the present invention

EXAMPLES

Production Example 1: Synthesis of Compound 10

[Formula 17]

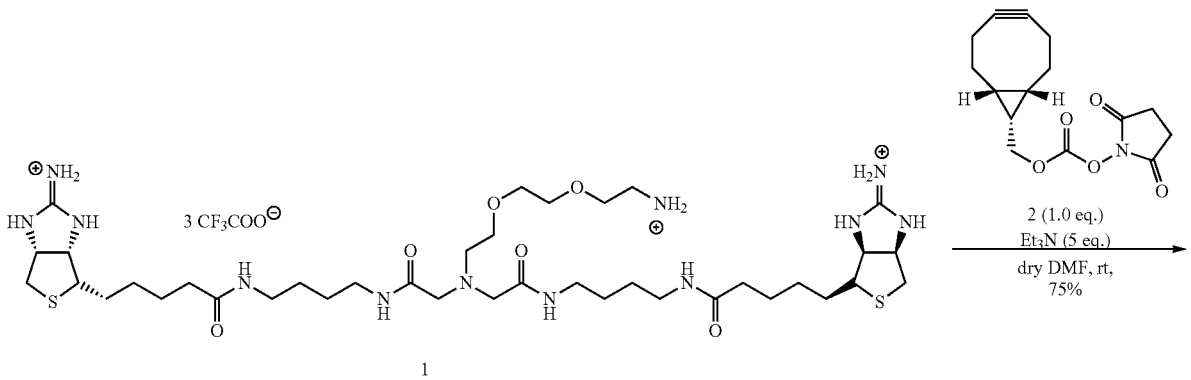

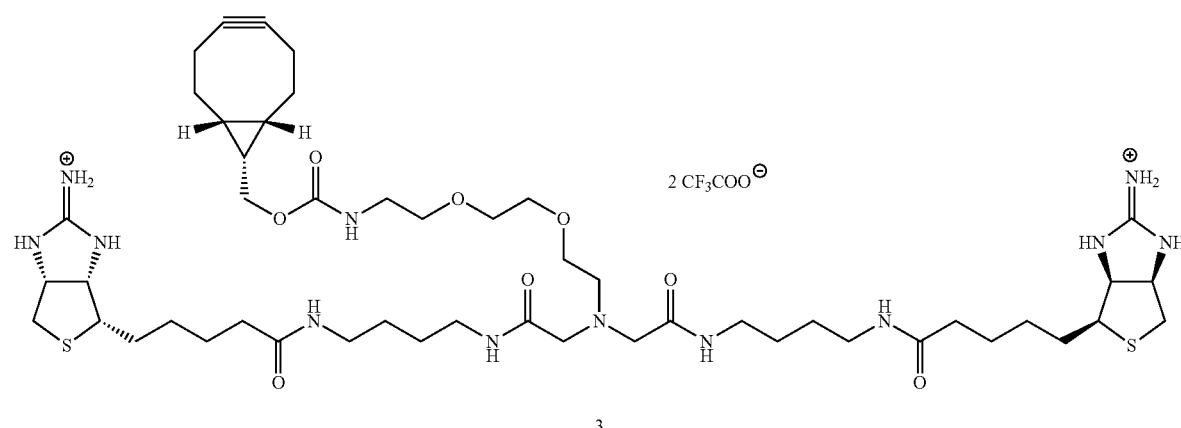

(1R,8S,9S)-Bicyclo[6.1.0]non-4-yn-9-ylmethyl N-succinimidyl carbonate 2 (1.0 mg, 3.4 μmol, Et₃N (1.7 mg, 17 μmol) and dehydrated DMF (500 μL) were added to Psyche J 1 (4.5 mg, 3.4 μmol, and the obtained mixture was then stirred at room temperature for 15 hours. Thereafter, the reaction mixture diluted with water to 2000 μL was purified by reversed phase HPLC (gradient 10% for 5 min; 10-60% for 20 min CH₃CN in a 0.1% trifluoroacetic acid aqueous solution, retention time=19.0 min YMC-Triart C18, flow rate=3.5 mL/min), so as to obtain a target compound 3 (3.2 mg, 75%, colorless).

¹H NMR (400 MHz, CD₃OD): δ4.72 (m, 2H), 4.52 (m, 2H), 4.12 (d, J=8.2 Hz, 2H), 3.97 (s, 4H), 3.79 (t, J=5.0 Hz, 2H), 3.62 (s, 4H), 3.53 (t, J=6.0 Hz, 2H), 3.39 (brs, 2H), 3.30-3.23 (m, 8H), 3.17 (t, J=6.0 Hz, 4H), 2.98 (dd, J=13.7, 4.6 Hz, 2H), 2.81 (d, J=13.7 Hz, 2H), 2.25-2.10 (m, 10H), 1.81-1.30 (m, 23H), 0.92 (t, J=10.1 Hz, 2H).

LRMS (ESI): m/z 1031.55 [M+H]⁺, 516.35 [M+2H]²⁺, 344.75 [M+3H]³⁺

[Formula 18]

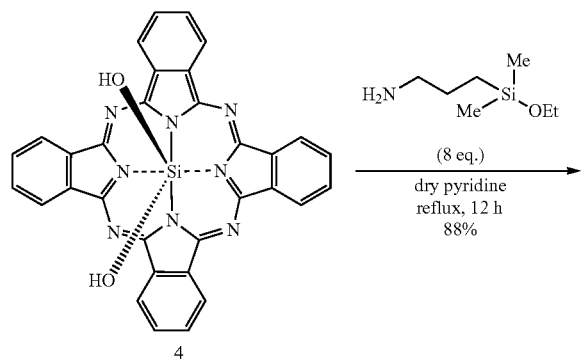

[Formula 19]

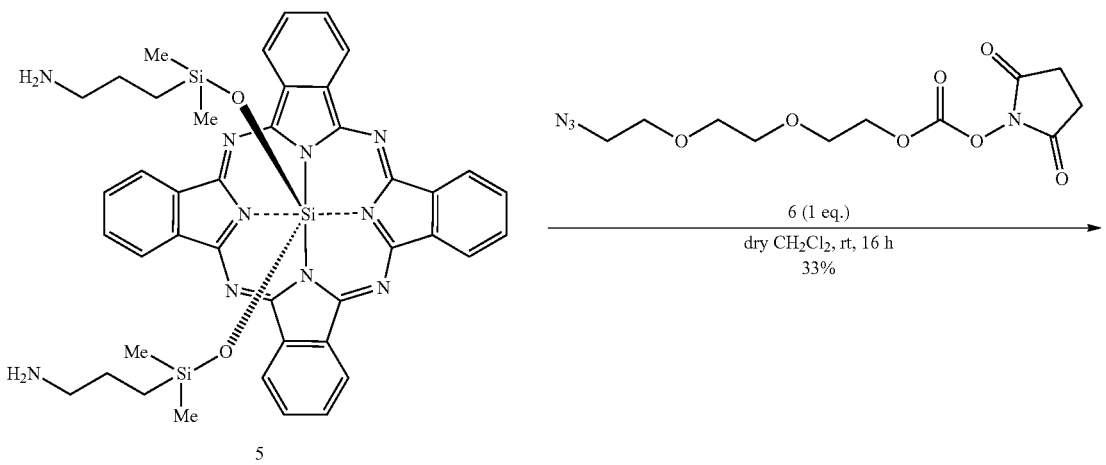

(3-Aminopropyl)dimethylethoxysilane (113 mg, 700 μmol and dehydrated pyridine (30 mL) were added to Silicon phthalocyanine dihydride 4 (50 mg, 87 μmol). The obtained mixture was stirred for 5 hours and was heated to reflux. The reaction mixture, from which the solvent had been distilled away under reduced pressure, was purified by column chromatography (gradient: 1% for 3 min; 1-10% for 15 min; 10-20% for 10 min CH₃OH in CH₂Cl₂, Yamazen Corporation Universal™ Column Amino 40 mm 60 Å 2.3×12.3 cm, 16 g, flow rate=10 mL/min), so as to obtain a target compound 5 (62 mg, 77 μmol, 88%, dark blue).

¹H NMR (500 MHz, CDCl₃): δ9.65 (dd, J=2.8 Hz, 5.7 Hz, 8H), 8.34 (dd, J=2.8 Hz, 5.7 Hz, 8H), 1.18 (t, J=7.6 Hz, 4H), −1.23 (m, 4H), −2.30 (m, 4H), −2.86 (s, 12H).

LRMS (ESI): m/z 805.30 [M+H]⁺

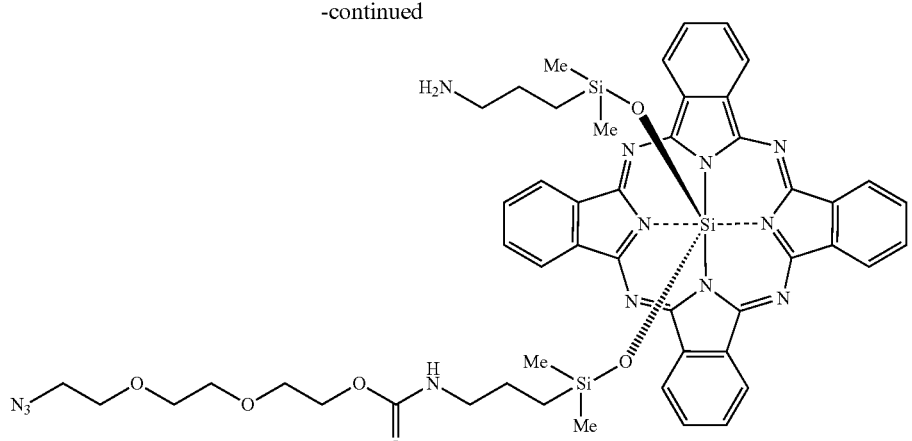

7

A dehydrated dichloromethane (3 mL) solution, in which the compound 5 (29 mg, 36 μmol) had been dissolved, was stirred, and thereafter, a dehydrated dichloromethane (2 mL) solution of a compound 6 (12 mg, 38 μmol) was slowly added into the reaction solution at room temperature. After that, the light was shielded with aluminum foil, and the mixed solution was then stirred at room temperature for 16 hours. The reaction mixture, from which the solvent had been distilled away under reduced pressure, was purified by column chromatography (gradient: 1% for 3 min; 1-5% for 15 min $CH_3OH$ in $CH_2Cl_2$, Yamazen Corporation Universal™ Column Amino 40 mm 60 Å 2.3×12.3 cm, 16 g, flow rate=10 mL/min), so as to obtain a target compound 7 (12 mg, 12 μmol, 33%, dark blue).

$^1$H NMR (500 MHz, $CDCl_3$): δ9.65 (dd, J=2.8 Hz, 5.7 Hz, 8H), 8.35 (d, J=2.8 Hz, 5.7 Hz, 8H), 4.08 (t, J=4.8 Hz, 2H), 3.73-3.60 (m, 8H), 3.39 (t, J=5.7 Hz, 2H), 1.76 (m, 2H), 1.18 (t, J=6.7 Hz, 2H), −1.23 (m, 4H), −2.30 (m, 4H), −2.86 (s, 12H).

LRMS (ESI): m/z 1006.85 [M+H]$^+$

[Formula 20]

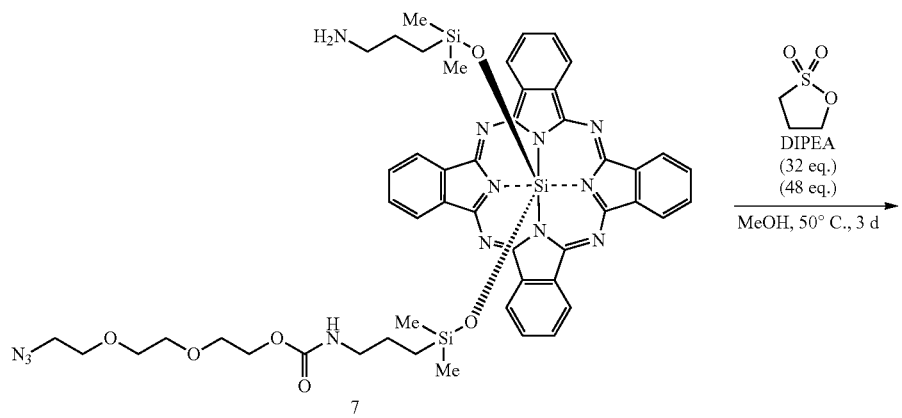

7

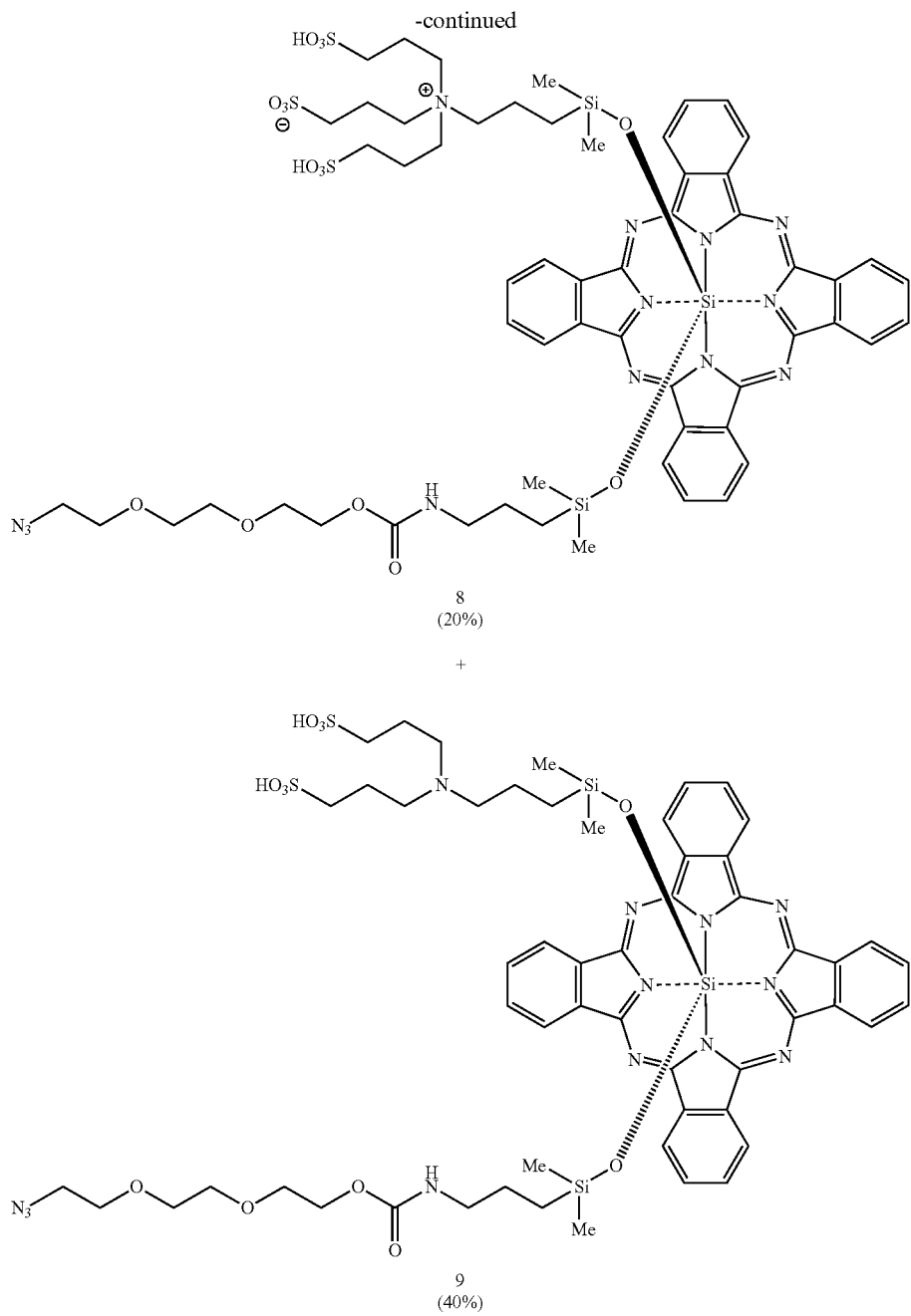

1,3-Propanesultone (19 mg, 0.16 μmol), DIPEA (30 mg, 0.23 μmol), and methanol (500 μL) were added to the compound 7 (4.8 mg, 4.8 μmol), the light was shielded with aluminum foil, and the obtained mixture was then stirred at 50° C. for 60 hours. Thereafter, the solvent was distilled away under reduced pressure, and the residue diluted with water/acetonitrile (1:1) to 3000 μL was then purified by reversed phase HPLC (gradient 50% for 5 min; 50-80% for 25 min; 80-100% for 10 min $CH_3CN$ in a 50 mM triethylammonium acetate aqueous solution (pH 7.0), retention time=15.8 (compound 8), 23.0 (compound 9) min, YMC-Triart C18, flow rate=3.5 mL/min), so as to obtain a target compound 8 (1.3 mg, 0.94 μmol, 20%, dark blue) and a target compound 9 (2.4 mg, 1.9 μmol, 40%, dark blue).

Compound 8: $^1$H NMR (500 MHz, $CD_3OD$): δ9.72 (dd, J=2.8 Hz, 5.7 Hz, 8H), 8.46 (dd, J=2.8 Hz, 5.7 Hz, 8H), 3.97 (t, J=4.8 Hz, 2H), 3.63-3.58 (m, 8H), 3.32 (m, 2H), 2.80-2.70 (m, 12H), 1.99 (t, J=6.7 Hz, 2H), 1.70 (m, 6H), 1.60 (t, J=6.7 Hz, 2H), −1.07 (m, 2H), −1.14 (m, 2H), −2.12 (m, 2H), −2.28 (m, 2H), −2.82 (s, 6H), −2.89 (s, 6H).

LRMS (ESI): m/z 1372.55 $[M+H]^+$

Compound 9: $^1$H NMR (500 MHz, $CD_3OD$): δ9.70 (dd, J=2.8 Hz, 5.7 Hz, 8H), 8.46 (dd, J=2.8 Hz, 5.7 Hz, 8H), 3.97 (t, J=4.8 Hz, 2H), 3.63-3.58 (m, 8H), 3.32 (m, 2H), 2.75 (t, J=6.7 Hz, 4H), 2.56 (brs, 4H), 1.71 (m, 6H), 1.60 (t, J=6.7 Hz, 2H), −1.00 (m, 2H), −1.14 (m, 2H), −2.15 (m, 2H), −2.27 (m, 2H), −2.83 (s, 6H), −2.89 (s, 6H).

LRMS (ESI): m/z 1249.80 $[M+H]^+$

[Formula 21]

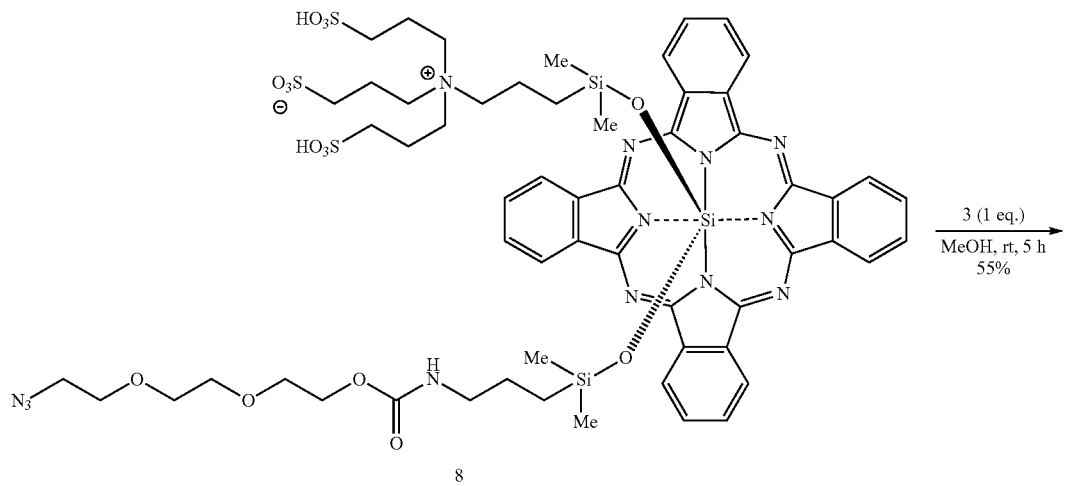

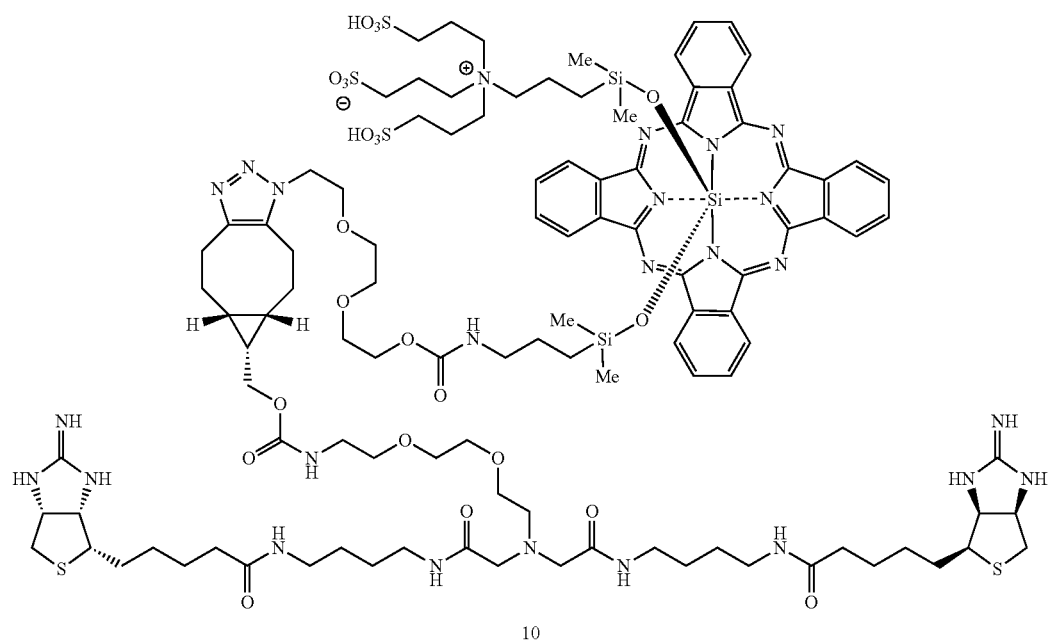

The compound 3 (1.3 mg, 1.0 μmol) and methanol (500 μL) were added to the compound 8 (1.6 mg, 1.0 μmol), the light was shielded with aluminum foil, and the obtained mixture was then stirred at room temperature for 5 hours. Thereafter, the reaction mixture diluted with water/acetonitrile (3:1) to 3000 μL was purified by reversed phase HPLC (gradient 30% for 5 min; 30-80% for 30 min; 80-100% for 8 min $CH_3CN$ in a 50 mM triethylammonium acetate aqueous solution (pH 7.0), retention time=26.5 min, YMC-Triart C18, flow rate=3.5 mL/min), so as to obtain a target compound 10 (1.3 mg, 0.55 μmol, 55%, dark blue). The thus obtained compound 10 is also referred to as Compound 1.

LRMS (ESI): m/z 1202.50 $[M+2H]^{2+}$

Production Example 2: Synthesis of Compound 11

[Formula 22]

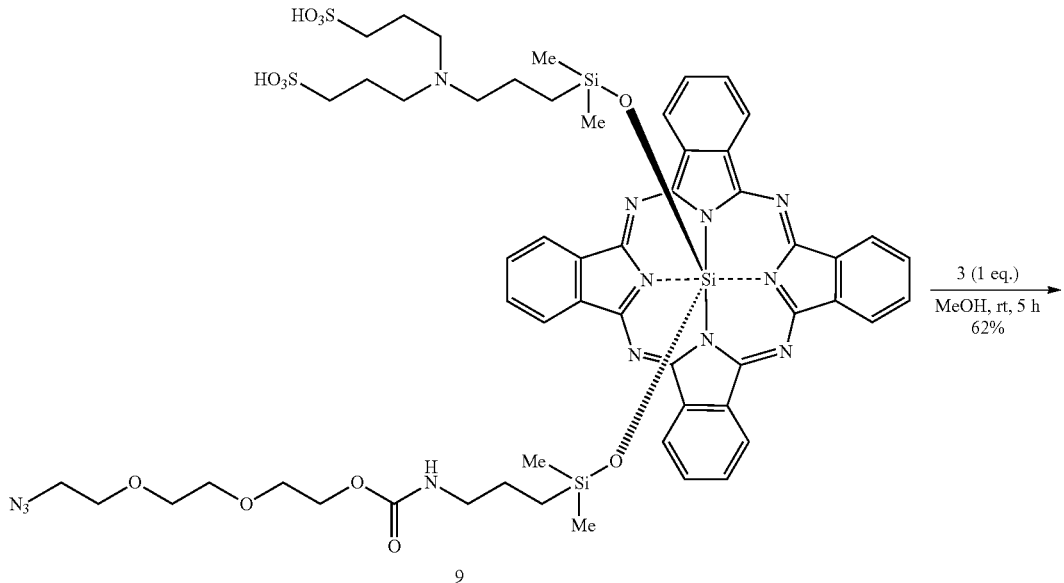

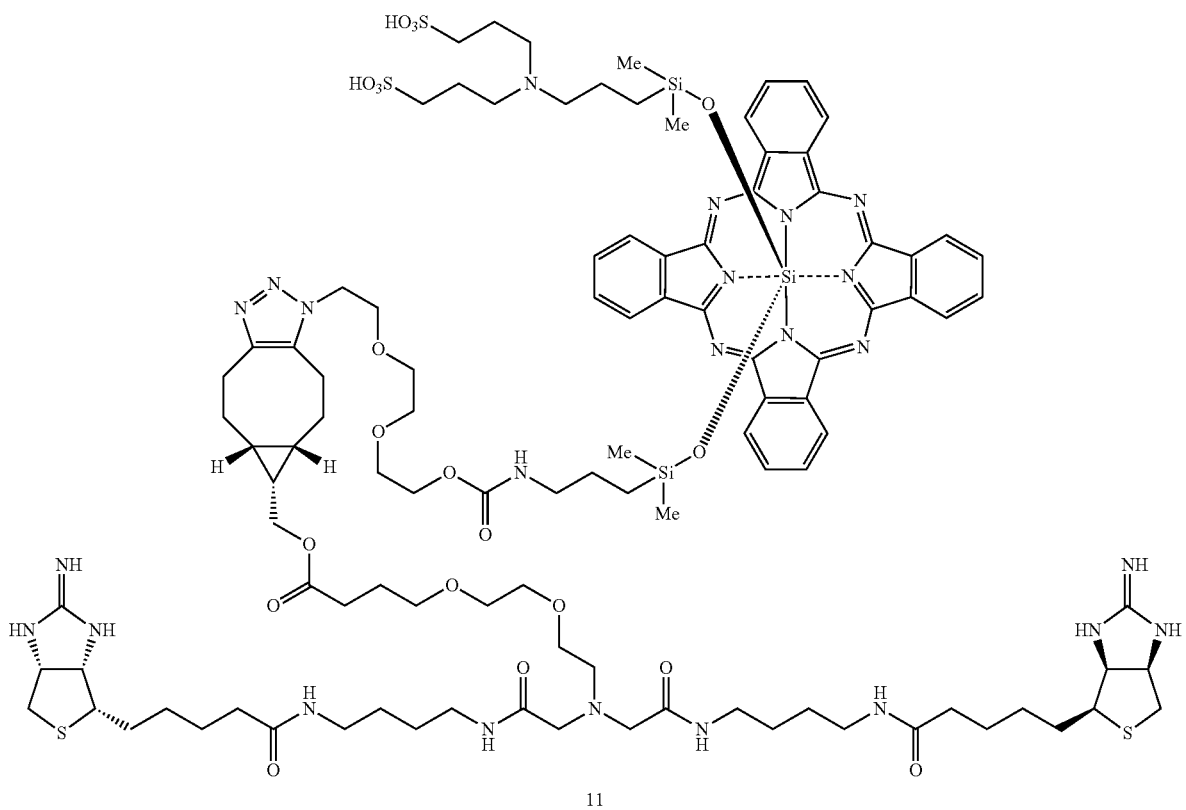

The compound 3 (1.5 mg, 1.1 μmol) and methanol (500 μL) were added to the compound 9 (1.5 mg, 1.1 μmol), the light was shielded with aluminum foil, and the obtained mixture was then stirred at room temperature for 5 hours. Thereafter, the reaction mixture diluted with water/acetonitrile (3:1) to 3000 μL was purified by reversed phase HPLC (gradient 30% for 5 min; 30-80% for 30 min; 80-100% for 8 min CH$_3$CN in a 50 mM triethylammonium acetate aqueous solution (pH 7.0), retention time=28.8 min, YMC-Triart C18, flow rate=3.5 mL/min), so as to obtain a target compound 11 (1.6 mg, 0.68 μmol, 62%, dark blue). The thus obtained compound 11 is also referred to as Compound 2.

LRMS (ESI): m/z 1141.65 [M+2H]$^{2+}$, 760.90 [M+3H]$^{3+}$

Production Example 3: Synthesis of Compound 13

[Formula 23]

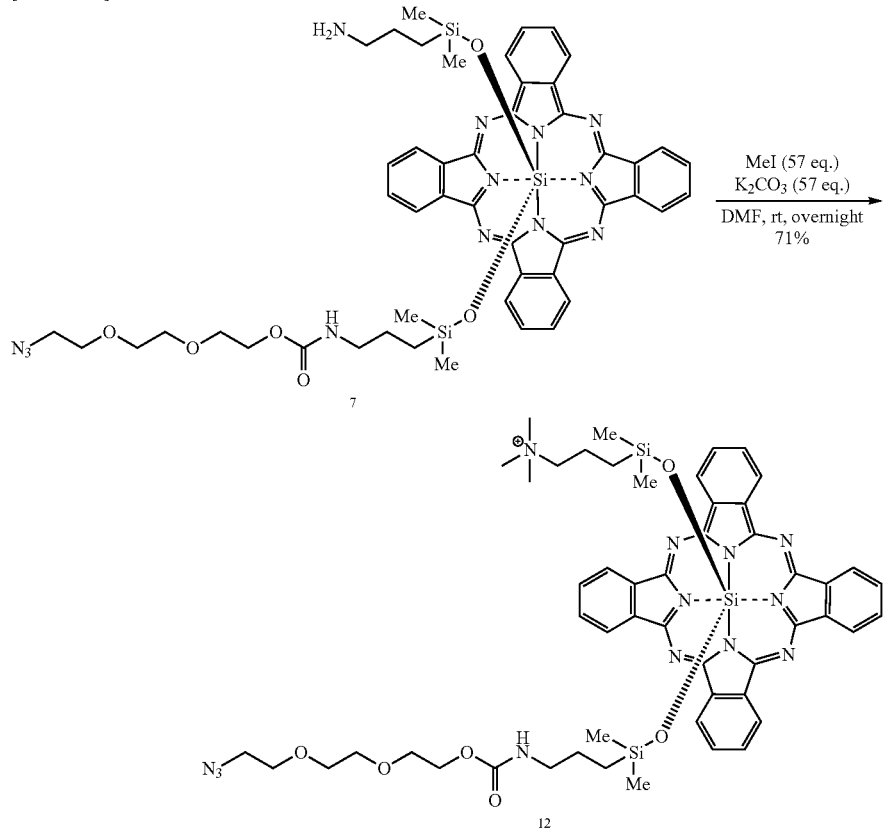

Methyl iodide (22.8 mg, 161 μmol), K$_2$CO$_3$ (22.2 mg, 161 μmol), and dimethyl formamide (500 μL) were added to the compound 7 (2.8 mg, 2.8 μmol), the light was shielded with aluminum foil, and the obtained mixture was then stirred at 50° C. for 60 hours. Thereafter, the solvent was distilled away under reduced pressure, and the residue diluted with water/acetonitrile (1:1) to 1000 μL was purified by reversed phase HPLC (gradient: 70% for 5 min; 70-100% for 25 min; CH$_3$CN in a 50 mM triethylammonium acetate aqueous solution (pH 7.0), retention time=21.5 min, YMC-Triart C18, flow rate=3.5 mL/min), so as to obtain a target compound 12 (2.1 mg, 2.0 μmol, 71%, dark blue).

$^1$H NMR (400 MHz, CD$_3$OD): δ9.68 (dd, J=2.8 Hz, 5.7 Hz, 8H), 8.44 (dd, J=2.8 Hz, 5.7 Hz, 8H), 3.96 (t, J=4.6 Hz, 2H), 3.63-3.58 (m, 8H), 3.31 (m, 2H), 2.44 (s, 9H), 1.94 (t, J=8.8 Hz, 2H), 1.59 (t, J=6.7 Hz, 2H), −1.16 (m, 4H), −2.14 (m, 2H), −2.28 (m, 2H), −2.84 (s, 6H), −2.89 (s, 6H).

LRMS (ESI): m/z 1048.30 [M]$^+$

[Formula 24]

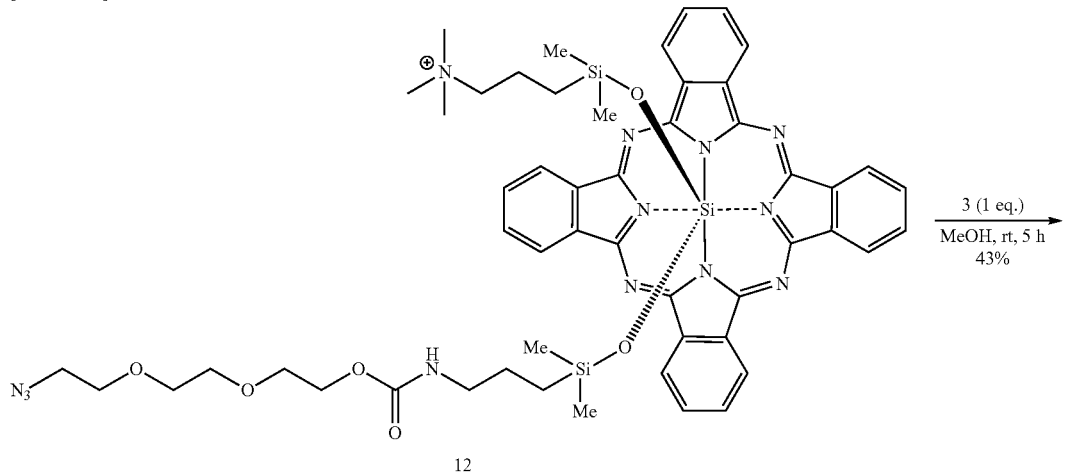

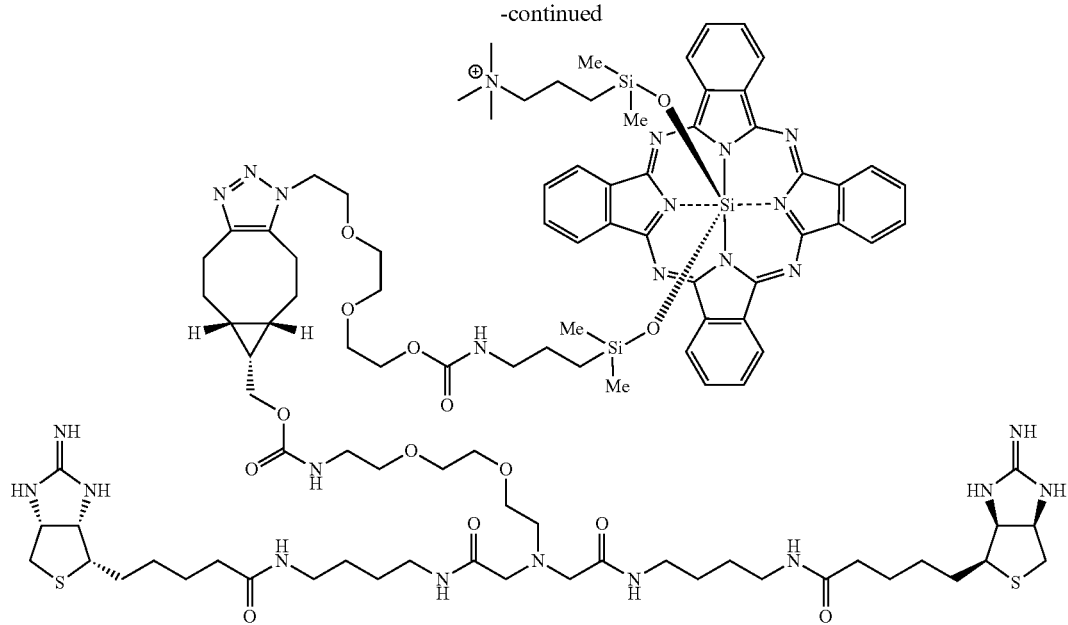

13

The compound 3 (1.3 mg, 1.0 μmol) and methanol (500 μL) were added to the compound 12 (1.0 mg, 1.0 μmol), the light was shielded with aluminum foil, and the obtained mixture was then stirred at room temperature for 5 hours. The reaction mixture, from which the solvent had been distilled away under reduced pressure, was purified by column chromatography (gradient 25% for 5 min; 50-100% for 20 min CH$_3$OH in CH$_2$Cl$_2$, Yamazen Corporation Universal™ Column Amino 40 mm 60 Å 1.8×11.4 cm, 7 g, flow rate=8 mL/min), so as to obtain a target compound 13 (0.92 mg, 0.43 μmol, 43%, dark blue). The thus obtained compound 13 is also referred to as Compound 4.

LRMS (ESI): m/z 694.05 [M+2H]$^{3+}$, 520.90 [M+3H]$^{4+}$

Production Example 4: Synthesis of Compound 14

[Formula 25]

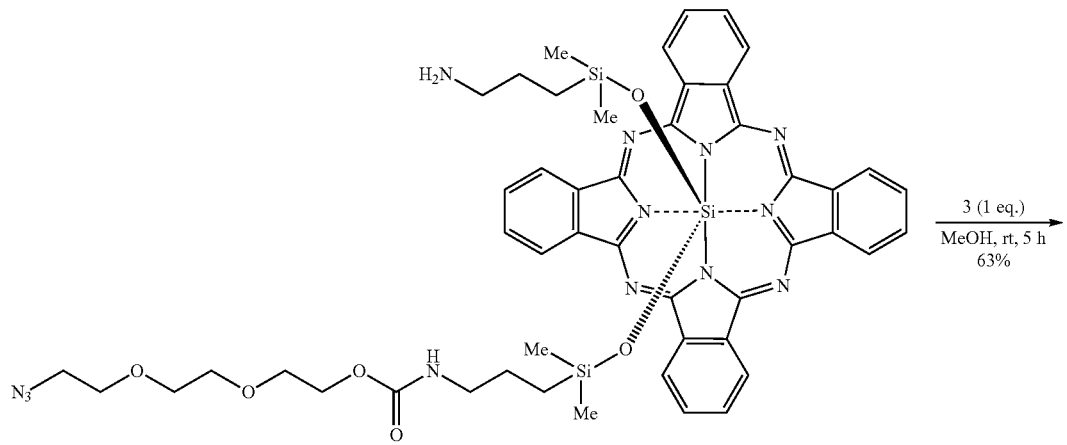

7

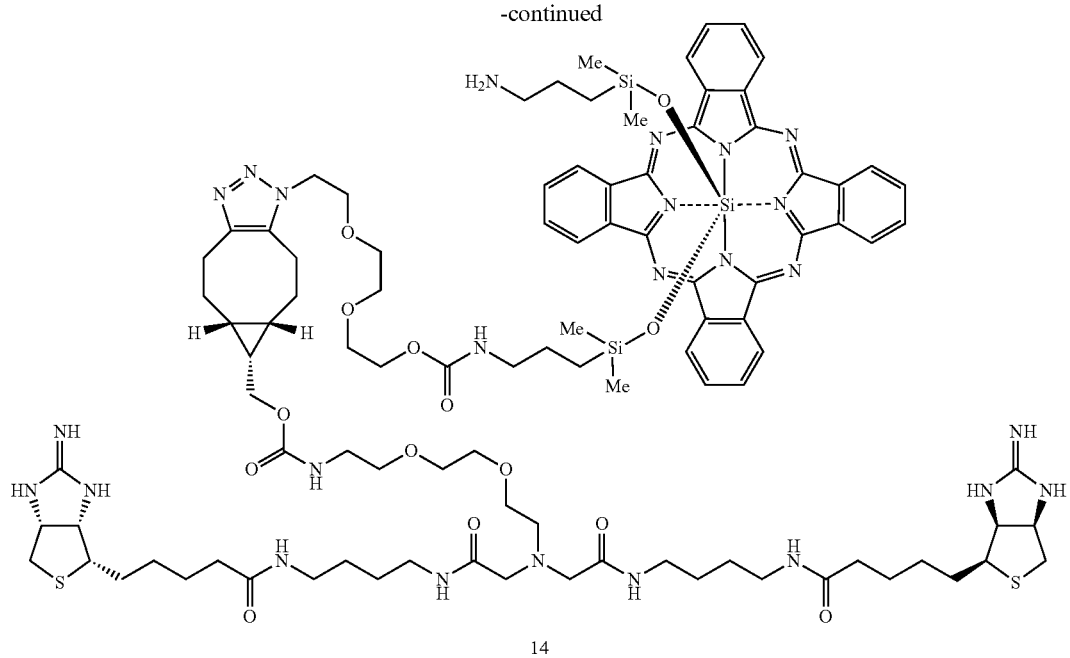

14

The compound 3 (3.6 mg, 2.7 μmol) and methanol (500 μL) were added to the compound 7 (2.7 mg, 2.7 μmol), the light was shielded with aluminum foil, and the obtained mixture was then stirred at room temperature for 5 hours. The reaction mixture, from which the solvent had been distilled away under reduced pressure, was purified by column chromatography (gradient 25% for 5 min; 50-100% for 20 min CH₃OH in CH₂Cl₂, Yamazen Corporation Universal™ Column Amino 40 mm 60 Å 1.8×11.4 cm, 7 g, flow rate=8 mL/min), so as to obtain a target compound 14 (3.5 mg, 1.7 μmol, 63%, dark blue). The compound 14 is also referred to as Compound 5.

LRMS (ESI): m/z 1019.25 $[M+2H]^{2+}$, 679.65 $[M+3H]^{3+}$, 510.00 $[M+4H]^{4+}$

Production Example 5: Synthesis of Compound 17

[Formula 26]

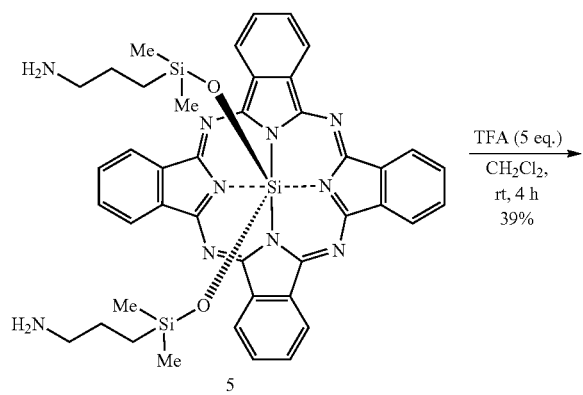

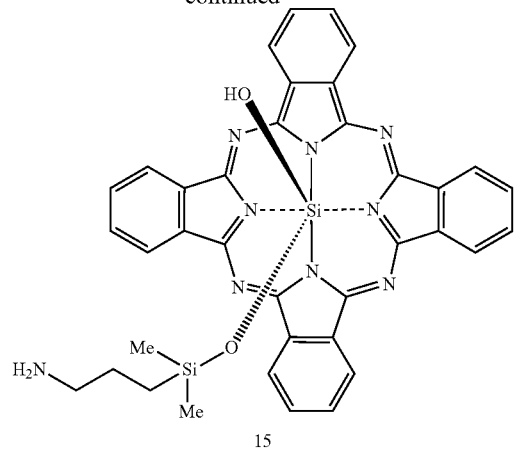

15

Trifluoroacetic acid (18.4 mg, 161 μmol) and dichloromethane (1.0 mL) were added to the compound 5 (19.0 mg, 23.0 μmol), the light was shielded with aluminum foil, and the obtained mixture was then stirred at room temperature for 4 hours. Thereafter, dichloromethane (10 mL), pyridine (1.0 mL), and water (10 mL) were added to the reaction mixture, and an organic layer was extracted. The organic layer, from which the solvent had been distilled away under reduced pressure, was purified by column chromatography (2% CH₃OH in CH₂Cl₂, Yamazen Corporation Universal™ Column Amino 40 mm 60 Å 1.8×11.4 cm, 7 g flow rate=8 mL/min), so as to obtain a target compound 15 (6.1 mg, 6.1 μmol, 39%, dark blue).

¹H NMR (500 MHz, CDCl₃): δ9.16 (m, 8H), 8.22 (d, J=1.9 Hz, 4.7 Hz, 8H), 0.98 (t, J=7.6 Hz, 2H), −1.47 (m, 2H), −2.51 (t, J=8.6 Hz, 2H), −2.86 (s, 6H).

[Formula 27]

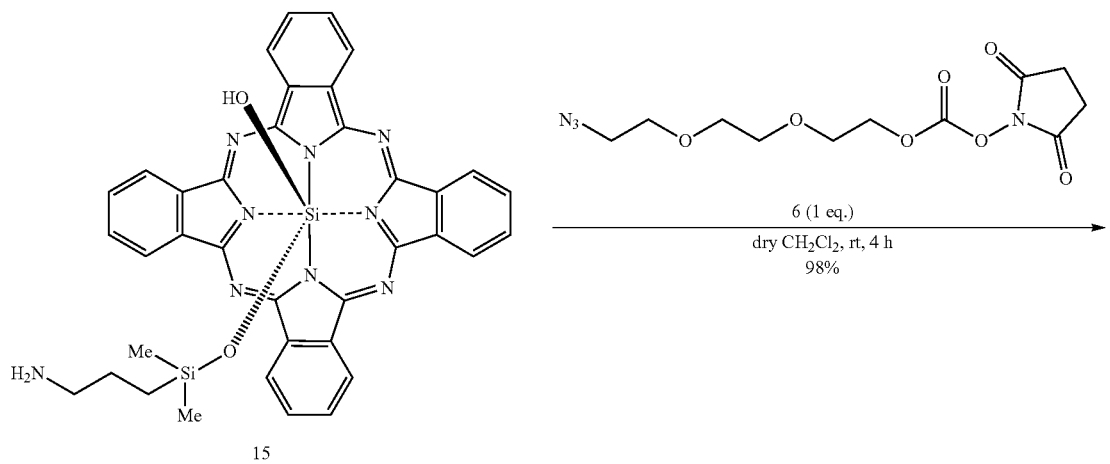

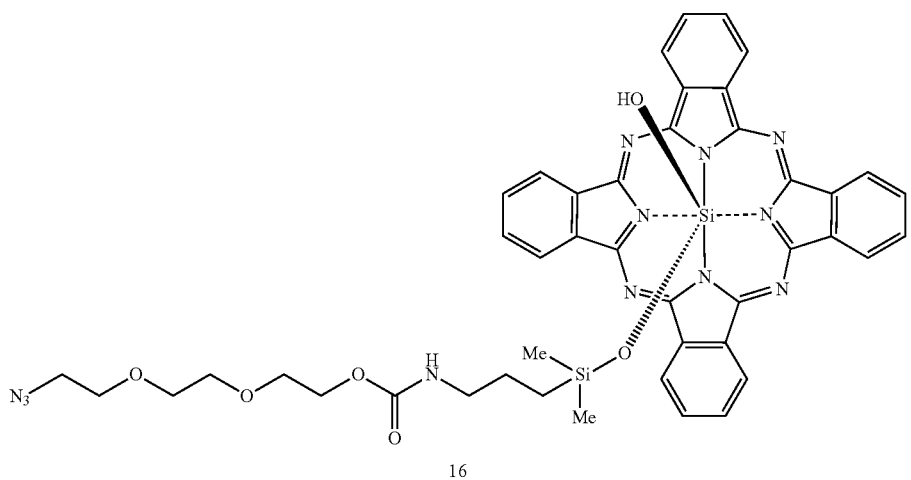

The compound 6 (1.2 mg, 3.8 μmol) and dehydrated dichloromethane (1.0 mL) were added to the compound 15 (2.6 mg 3.8 μmol), the light was shielded with aluminum foil, and the obtained mixture was then stirred at room temperature for 4 hours. The reaction mixture, from which the solvent had been distilled away under reduced pressure, was purified by column chromatography (gradient: 50-100% AcOEt in n-hexane, Yamazen Corporation Universal™ Premium Silica Gel 30 mm 60 Å 1.8×11.4 cm, 7 g, flow rate=8 mL/min), so as to obtain a target compound 16 (3.3 mg, 3.7 μmol, 98%, dark blue).

$^1$H NMR (500 MHz, CDCl$_3$): δ9.28 (brs, 8H), 8.25 (m, 8H), 4.00 (m, 2H), 3.67 (m, 8H), 3.37 (t, J=4.8 Hz, 2H), 1.73 (m, 2H), −1.38 (m, 2H), −2.30 (m, 2H), −2.86 (s, 6H).

[Formula 28]

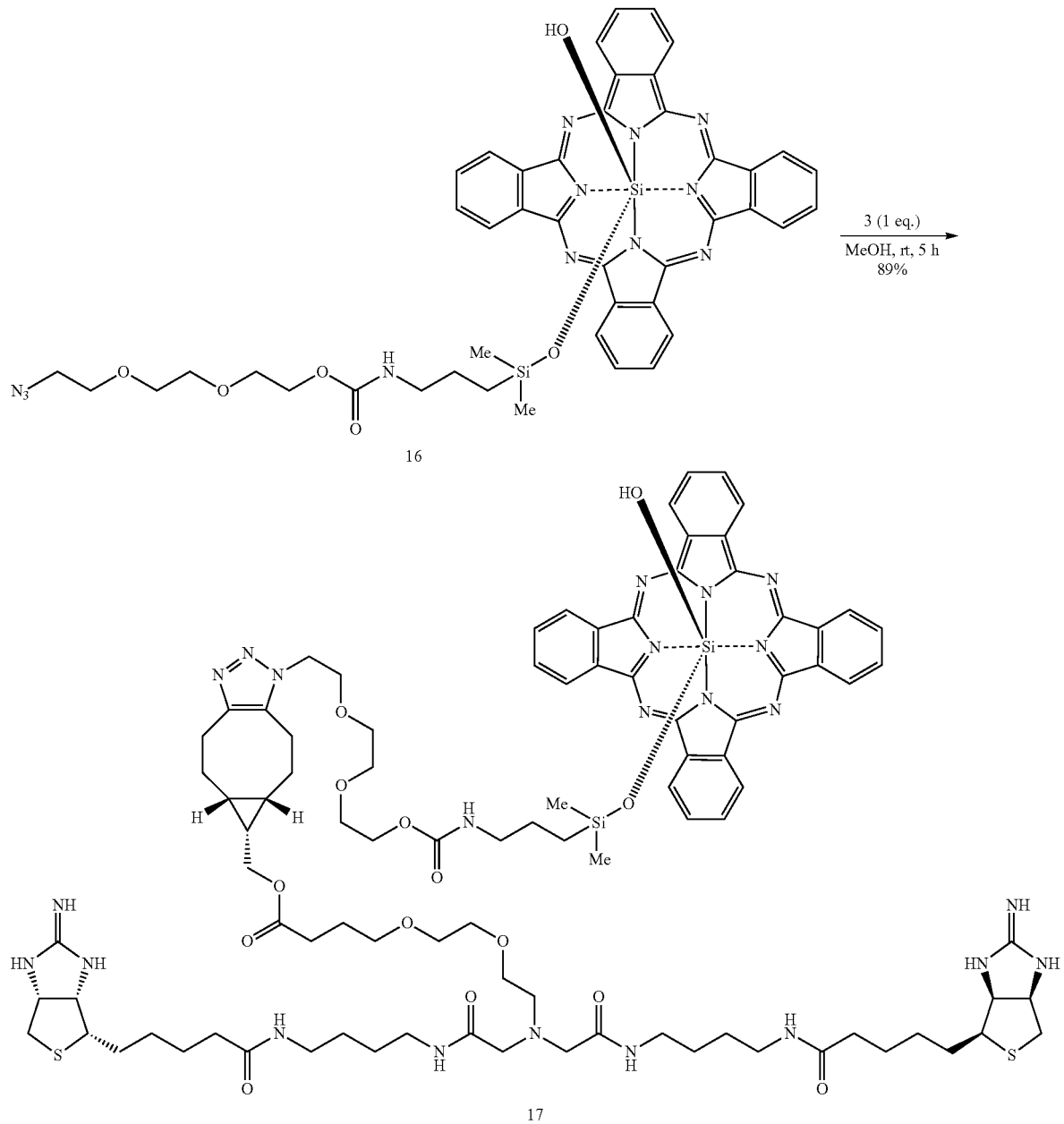

The compound 3 (2.5 mg, 1.9 μmol) and methanol (500 μL) were added to the compound 16 (1.9 mg, 2.1 μmol), the light was shielded with aluminum foil, and the obtained mixture was then stirred at room temperature for 5 hours. The reaction mixture, from which the solvent had been distilled away under reduced pressure, was purified by column chromatography (gradient: 10% for 5 min; 25% for 7 min CH$_3$OH in CH$_2$Cl$_2$, Yamazen Corporation Universal™ Column Amino 40 mm 60 Å 1.8×11.4 cm, 7 g, flow rate=8 mL/min), so as to obtain a target compound 17 (3.3 mg, 1.7 μmol, 89%, dark blue). The thus obtained compound 17 is also referred to as Compound 3.

LRMS (ESI): m/z 952.55 [M–H$_2$O+2H]$^{2+}$, 635.85 [M–H$_2$O+3H]$^{3+}$, 476.80 [M–H$_2$O+4H]$^{4+}$

Example 1: Expression and Purification of CEA-V2122 Protein

V2122 is the mutant streptavidin described in Example 3 of International Publication WO2015/125820 (SEQ ID NO: 4 shown in International Publication WO2015/125820). The amino acid sequence of V2122 (a sequence having a 6×His tag (SEQ ID NO: 14) at the C-terminus) is as set forth in SEQ ID NO: 1 in the sequence listing.

scFv-V2122 is prepared by binding a single-chain antibody (scFv) against CEACAM5 with the above-described V2122. This scFv-type anti-CEACAM5 antibody is an scFv sequence described in a patent document U.S. Pat. No. 7,626,011B2. The amino acid sequence of the scFv-type anti-CEACAM5 antibody is as set forth in SEQ ID NO: 2 in the sequence listing. In addition, the amino acid sequence of CEA-V2122 prepared by binding the scFv-type anti-CEACAM5 antibody with V2122 via an amino acid linker (GGGGSGGGG) (SEQ ID NO: 7) is as set forth in SEQ ID NO: 3 in the sequence listing.

For the expression of a CEA-V2122 fusion protein, the DNA codon of a CEA-V2122 gene sequence, in which a pelB signal for secretion and expression in *Escherichia coli* had been incorporated into the N-terminus and a 6×His-Tag sequence (SEQ ID NO: 14) had been incorporated into the C-terminus, was optimized for *Escherichia coli*, thereby synthesizing an artificial gene. This amino acid sequence is as set forth in SEQ ID NO: 4 in the sequence listing, and the DNA sequence is as set forth in SEQ ID NO: 5 in the sequence listing. Moreover, an outline of a domain structure is shown in FIG. 1.

As a specific protein expression vector, a vector prepared by incorporating a chaperone skp gene into MCS2 of a pETDuet1 vector was used. Regarding the skp gene, the DNA codon was optimized for *Escherichia coli* based on the amino acid sequence as set forth in SEQ ID NO: 6 in the sequence listing, thereby synthesizing an artificial gene. The synthesized skp gene was amplified by PCR, using the primers (AAGGAGATATACATATGGATAAAATTGC-CATTGTTAATAT (SEQ ID NO: 8), and TTGAGATCTGC-CATATGTTATTTCACTTGTTTCAGAACG (SEQ ID NO: 9)), and the amplified gene was then cloned into MCS2 of the pETDue1 vector linearized with the restriction enzyme Ndel, using In-Fusion HD Cloning Kit, so as to obtain pETDuet_skp. Subsequently, the CEA-V2122 gene was incorporated into MCS1 of pETDuet_skp. Specifically, the artificially synthesized CEA-V2122 gene was amplified by PCR, using the primers (AGAAGGAGATATACCAT-GAAATATCTGCTGCCGAC (SEQ ID NO: 10), and CGCCGAGCTCGAATTTTAATGATGGTGATGATGATG (SEQ ID NO: 11)). Moreover, pETDuet_skp was linearized by PCR, using the primers (GGTATATCTCCTTCT-TAAAGTTAAAC (SEQ ID NO: 12), and AAT-TCGAGCTCGGCGCGCCTGCAG (SEQ ID NO: 13)). The CEA-V2122 amplified by PCR and the linearized pETDuet_skp were subjected to cloning using In-Fusion HD Cloning Kit. The cloned vector was confirmed by sequencing, in terms of the gene sequence incorporated therein, and thereafter, it was referred to as pETDuet_CEA-V2122_skp.

For the expression of the protein, pETDuet_CEA-V2122_skp was transformed into BL21(DE3) (Nippon Gene Co., Ltd.), which was then pre-cultured in 2×YT medium (SIGMA-ADLRICH) at 37° C. overnight. The medium used in the pre-culture was added to a new medium for 100-fold dilution, and culture was then carried out at 37° C., until OD (600 nm) became 0.5 to 2.0. Subsequently, IPTG was added to the culture to a final concentration of 0.5 mM, and the obtained mixture was then cultured at 37° C. for 4 hours. Thereafter, a culture supernatant was recovered and was then preserved at 4° C.

The CEA-V2122 protein was roughly purified according to a batch method utilizing 6×His-Tag (SEQ ID NO: 14) added to the C-terminus. Specifically, cOmplete His-Tag Purification Resin equilibrated with buffer A (50 mM Tris-HCl, 0.2 M NaCl, 1 mM EDTA, and 5 mM Imidazole; pH 8.0) was added to the culture supernatant preserved at 4° C. The obtained mixture was stirred for 2 hours to overnight at 4° C., so that the protein was allowed to bind to the resin. Subsequently, the resin was recovered into a column, and a 20 column volume of washing operation was performed with buffer A Thereafter, a roughly purified product of CEA-V2122 was recovered by elution with buffer B (50 mM Tris-HCl, 0.2 M NaCl, 1 mM EDTA, and 400 mM Imidazole; pH 8.0).

Subsequently, the roughly purified product was purified using a Protein L column. Specifically, 1 mL of Capto L (GE Healthcare Life Sciences) was filled into a PD-10 column, and was then equilibrated with 10 column volume of PBS, and the aforementioned roughly purified product was then applied thereto. Thereafter, the resultant was washed with 10 column volume of PBS, was then eluted with 10 mM glycine hydrochloride (pH 2.0), and was then subjected to centrifugal concentration using Vivaspin Turbo 15 (MWCO 100, 000). Moreover, using PD-10 (GE Healthcare Life Science), the buffer was replaced with PBS, and centrifugal concentration was further carried out using Vivaspin Turbo 4 (MWCO 100,000) to obtain a finally purified product After completion of SDS-PAGE electrophoresis, the purity of tetramer CEA-V2122 was assayed by CBB staining. The results are shown in FIG. 2. As an SDS-PAGE gel, Mini-PROTEAN TGX 4-15% (Bio-Rad) was used, and as a CBB staining solution, Bullet CBB Stain One (Ready To Use) (Nacalai Tesque, Inc.) was used.

From FIG. 2, it was confirmed that the purified CEA-V2122 comprises an approximately 150 kDa tetramer as a main component.

Example 2: Evaluation of Performance of CEA-V2122 by SPR

The affinity of CEA-V2122 for the antigen CEACAM5 was evaluated using a surface plasmon resonance (SPR) measuring device, Biacore T200 (GE Healthcare Life Sciences). Specifically, Recombinant Human CEACAM-5/CD66e Protein, CF (R & D SYSTEMS) was immobilized on Sensor Chip CMS (GE Healthcare Life Sciences) using an amine-coupling kit (GE Healthcare Life Sciences). The final amount of the ligand immobilized was 279 RU. Moreover, with regard to the purified CEA-V2122, two-fold serial dilutions from 1E-08 M to 6.25E-10 M were prepared as analytes. Regarding interaction analysis, data were obtained by single-cycle kinetics analysis. Using Biacore T200 Evaluation Software, version 2.0, the obtained data were subjected to curve fitting in a bivalent analysis mode, and the following values were obtained: ka1=3.208E+5, and kd1=3.461E-7. Moreover, since evaluation can be carried out at $K_D$=kd1/ka1 in the bivalent analysis, the evaluation value $K_D$=kd1/ka1=3.461E-7/3.208E+5=1.078E-12 was obtained. These results are shown in FIG. 3.

From the $K_D$ value in the sensorgram shown in FIG. 3, it was confirmed that CEA-V2122 strongly binds to CEACAM5.

Furthermore, the interaction between CEA-V2122 and a modified biotin was also analyzed using Biacore T200. The modified biotin was specifically the title compound 14 described in Example 1 of International Publication WO2018/07239. In addition, the analysis method was specifically as follows. That is, an amine-coupling kit was used, a target value was set to be 5000 RU, and the purified CEA-V2122 was immobilized on Sensor Chip CMS. With regard to the concentrations of the analytes, 5 types of two-fold serial dilutions from 1E-08 M to 6.25E-10 M were used. Regarding interaction analysis, data were obtained by single-cycle kinetics analysis. Using Biacore T200 Evaluation Software, version 2.0, the obtained data were subjected to curve fitting in a bivalent analysis mode, and the following values were obtained: ka1=3.792E+4, and kd1=4.424E-6. Moreover, since evaluation can be carried out at $K_D$=kd1/ ka1 in the bivalent analysis, the evaluation value $K_D$=kd1/ka1=3.792E+4/4.424E−6=1.167E−10 was obtained. These results are shown in FIG. 4.

From the $K_D$ value in the sensorgram shown in FIG. 4, it was confirmed that CEA-V2122 strongly binds to a modified biotin.

Example 3: Cell Staining of CEACAM5-Expressing Cell Line Using FITC-Labeled CEA-V2122

In order to stain a CEACAM5 expression-positive cancer cell line, FITC labeling was carried out on the cell line, using 100 μg of a purified CEA-V2122 protein. Specifically, labeling was carried out using Fluorescein Labeling Kit-NH₂ (DOJINDO LABORATORIES) in accordance with the dosage and administration described in the operating manual included with the kit, and the obtained product was defined to be CEA-V2122-FITC. Specific staining of the CEACAM5 expression-positive cancer cell line is as follows. That is, CEACAM5-positive human stomach cancer-derived MKN-45 cells and CEACAM5-negative human colon cancer-derived DLD1 cells were each seeded on a CELLSTAR, μClear, 96-well plate (Greiner) to a cell density of $2.0 \times 10^4$ cells/well, and thereafter, the cells were cultured overnight. Subsequently, a culture solution containing 20 nM CEA-V2122-FITC and 1 μM Hoechist was added to the 96-well plate to a concentration of 100 μL/well, and the obtained mixture was then reacted at 4° C. for 30 minutes. Thereafter, each image was taken using In Cell Analyzer 6000 (GE Healthcare Life Sciences). The results are shown in FIG. 5 and FIG. 6.

From the results shown in FIG. 5, it was confirmed that CEA-V2122-FITC specifically recognizes CEACAM5 on the surface of the cell membrane. In addition, from the results shown in FIG. 6, it was confirmed that after CEA-V2122-FITC has bound to CEACAM5, the CEACAM5 stays on the surface of the cell membrane.

Example 4: In Vitro Cytotoxicity Test Using CEA-V2122 and Photoactivatable Compound-Labeled Modified Biotins A cytotoxicity test was carried out using photoactivatable compound-labeled modified biotins (namely, Compound 1 (compound 10), Compound 2 (compound 11), Compound 3 (compound 17), Compound 4 (compound 13), and Compound 5 (compound 14)). Specifically, as shown in FIG. 5, CEA-positive MKN45 cells and CEA-negative DLD1 cells were seeded on a 96-well plate for cell culture, so that the cell count became $5 \times 10^3$ cells/well and the amount of the culture solution became 100 μL/well, and thereafter, the cells were cultured overnight. A solution containing a complex of CEA-V2122 and a photoactivatable compound-labeled modified biotin was prepared by mixing CEA-V2122 and each Compound to a molar ratio of 1:2, and then incubating the mixture at room temperature for 10 minutes. Thereafter, the concentration of the reaction solution was adjusted with a culture solution, so that the final concentration of CEA-V2122 became 5 μg/mL. Regarding serial dilutions, 5 μg/mL was set to be an initial concentration, and 5-fold serial dilutions (5.0 μg/mL, 1.0 μg/mL, and 0.2 μg/mL) were prepared. Besides, a medium alone that contained no complex was used as a control.

Subsequently, a cell culture solution that had been cultured overnight was discarded, and the prepared complex serial dilution solutions (5.0 μg/mL, 1.0 μg/mL, and 0.2 μg/mL) were each added to an amount of 100 μL/well. Twenty-four hours after addition of the complex, the cells were irradiated with a light, using LED emitting a light having a wavelength of 690±10 nm, so that the irradiation energy became 100 J/cm². Thereafter, the cells were cultured for 24 hours, and thereafter, a comparison was made in terms of the number of surviving cells, using Cell Counting Kit-8 (DOJINDO LABORATORIES). The dosage and administration were determined in accordance with the instruction manuals included with the kit, and after addition of the reagent, the mixture was incubated for 1.5 hours at 37° C., in a CO₂ incubator. Thereafter, the absorbance at 450 nm was measured, and a mean value was then calculated, followed by background collection. The control was set to be 100%, and the ratio of cell proliferation to the control under each condition was calculated. The results regarding the MNK45 cells are shown in FIG. 7, and the results regarding the DLD1 cells are shown in FIG. 8. In addition, the error bar in the figures indicates a standard deviation. From these results, it was confirmed that the reactions other than the reaction of Compound 5 (5 μg/mL) are antigen-specific, antibody concentration-dependent reactions.

SEQ ID NO: 1
AEAGITGTWSDQLGDTFIVTAGADGALTGTYENAVGGAESRYVLTGRYDSA

PATDGSGTALGWTVAWKNNSKNAHSATTWSGQYVGGADAKINTQWLLTSGT

TNANAWKSTLVGHDTFTKVKPSAASHHHHHH (sm3E-scFv sequence)
SEQ ID NO: 2
QVKLEQSGAEVVKPGASVKLSCKASGFNIKDSYMHWLRQGPGQRLEWIGWI

DPENGDTEYAPKFQGKATFTTDTSANTAYLGLSSLRPEDTAVYYCNEGTPT

GPYYFDYWGQGTLVTVSSGGGGSGGGGSGGGGSENVLTQSPSSMSVSVGDR

VNIACSASSSVPYMHWLQQKPGKSPKLLIYLTSNLASGVPSRFSGSGSGTD

YSLTISSVQPEDAATYYCQQRSSYPLTFGGGTKLEIK

SEQ ID NO: 3
QVKLEQSGAEVVKPGASVKLSCKASGFNIKDSYMHWLRQGPGQRLEWIGW

IDPENGDTEYAPKFQGKATFTTDTSANTAYLGLSSLRPEDTAVYYCNEGTP

TGPYYFDYWGQGTLVTVSSGGGGSGGGGSGGGGSENVLTQSPSSMSVSVGD

RVNIACSASSSVPYMHWLQQKPGKSPKLLIYLTSNLASGVPSRFSGSGSGT

DYSLTISSVQPEDAATYYCQQRSSYPLTFGGGTKLEIKGGGGSGGGGAEAG

ITGTWSDQLGDTFIVTAGADGALTGTYENAVGGAESRYVLTGRYDSAPATD

GSGTALGWTVAWKNNSKNAHSATTWSGQYVGGADAKINTQWLLTSGTTNAN

AWKSTLVGHDTFTKVKPSAASHHHHHH

SEQ ID NO: 4
MKYLLPTAAAGLLLLAAQPAMAQVKLEQSGAEVVKPGASVKLSCKASGFNI

KDSYMHWLRQGPGQRLEWIGWIDPENGDTEYAPKFQGKATFTTDTSANTAY

LGLSSLRPEDTAVYYCNEGTPTGPYYFDYWGQGTLVTVSSGGGGSGGGGSG

GGGSENVLTQSPSSMSVSVGDRVNIACSASSSVPYMHWLQQKPGKSPKLLI

YLTSNLASGVPSRFSGSGSGTDYSLTISSVQPEDAATYYCQQRSSYPLTFG

GGTKLEIKGGGGSGGGGAEAGITGTWSDQLGDTFIVTAGADGALTGTYENA

VGGAESRYVLTGRYDSAPATDGSGTALGWTVAWKNNSKNAHSATTWSGQYV

GGADAKINTQWLLTSGTTNANAWKSTLVGHDTFTKVKPSAASHHHHHH

SEQ ID NO: 5

ATGAAATATCTGCTGCCGACCGCAGCAGCGGGTCTGCTGCTGCTGGCAGCA
CAGCCTGCAATGGCACAGGTTAAACTGGAACAGAGCGGTGCCGAAGTTGTT
AAACCGGGTGCAAGCGTTAAACTGAGCTGTAAAGCAAGCGGCTTTAACATC
AAAGATAGCTATATGCATTGGCTGCGTCAGGGTCCGGGTCAGCGTCTGGAA
TGGATTGGTTGGATTGATCCGGAAAATGGTGATACCGAATATGCACCGAAA
TTTCAGGGTAAAGCAACCTTTACCACCGATACCAGCGCAAATACCGCATAT
CTGGGTCTGAGCAGCCTGCGTCCGGAAGATACCGCAGTGTATTATTGTAAT
GAAGGCACCCCGACCGGTCCGTATTATTTCGATTATTGGGGTCAGGGCACC
CTGGTTACCGTTAGCAGCGGTGGTGGTGGTAGTGGTGGCGGTGGTTCAGGC
GGTGGCGGTAGCGAAAATGTTCTGACCCAGAGCCCGAGCAGCATGAGCGTT
AGCGTTGGTGATCGTGTTAATATTGCATGTAGCGCAAGCAGCAGCGTTCCG
TACATGCACTGGCTGCAGCAGAAACCGGGTAAAAGCCCGAAACTGCTGATT
TATCTGACCAGCAATCTGGCAAGCGGTGTTCCGAGCCGTTTTAGCGGTAGC
GGTAGTGGCACCGATTATAGCCTGACCATTAGCAGCGTGCAGCCTGAAGAT
GCAGCAACCTATTATTGTCAGCAGCGTAGCAGTTATCCGCTGACCTTTGGT
GGTGGCACCAAACTGGAAATTAAAGGGGGTGGTGGCTCAGGTGGCGGAGGT
GCAGAAGCAGGTATTACCGGTACATGGTCAGATCAGCTGGGTGATACCTTT
ATTGTTACCGCAGGCGCAGATGGTGCACTGACCGGCACCTATGAAAATGCA

GTTGGTGGTGCAGAAAGCCGTTATGTGCTGACCGGTCGTTATGATAGCGCA
CCGGCAACCGATGGTAGCGGCACCGCACTGGGTTGGACCGTTGCATGGAAA
AATAACAGCAAAAATGCACATAGCGCAACCACCTGGTCAGGTCAGTATGTG
GGTGGTGCCGATGCCAAAATTAACACCCAGTGGCTGCTGACCAGCGGTACA
ACCAATGCAAATGCCTGGAAAAGTACCCTGGTTGGTCATGATACATTCACC
AAAGTTAAACCGAGCGCAGCAAGCCATCATCATCACCATCATTAA

SEQ ID NO: 6

MDKIAIVNMGSLFQQVAQKTGVSNTLENEFKGRASELQRMETDLQAKMKKL
QSMKAGSDRTKLEKDVMAQRQTFAQKAQAFEQDRARRSNEERGKLVTRIQT
AVKSVANSQDIDLVVDANAVAYNSSDVKDITADVLKQVK

SEQ ID NO: 7

GGGGSGGGG

SEQ ID NO: 8

AAGGAGATATACATATGGATAAAATTGCCATTGTTAATAT

SEQ ID NO: 9

TTGAGATCTGCCATATGTTATTTCACTTGTTTCAGAACG

SEQ ID NO: 10

AGAAGGAGATATACCATGAAATATCTGCTGCCGAC

SEQ ID NO: 11

CGCCGAGCTCGAATTTTAATGATGGTGATGATGATG

SEQ ID NO: 12

---

The invention claimed is:

1. A complex comprising (a) a compound represented by the following formula (1) or a salt thereof:

[Formula 1]

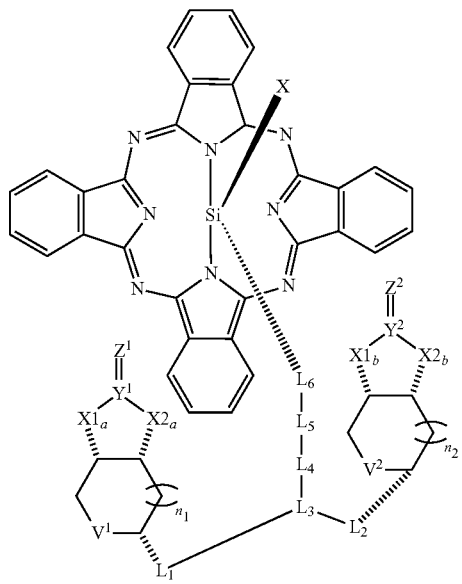

wherein

X represents a substituent having a hydrophilic group, a cationic group or an amino group at the terminus thereof, or —OH, X1a, X1b, X2a and X2b each independently represent O or NH, $Y^1$ and $Y^2$ each independently represent C or S, $Z^1$ and $Z^2$ each independently represent O, S or NH, $V^1$ and $V^2$ each independently represent S or $S^+$—$O^-$, n1 and n2 each independently represent an integer of 0 or 1, $L_1$ and $L_2$ each independently represent a divalent linking group, $L_3$ represents a trivalent linking group, $L_4$, $L_5$, and $L_6$ each independently represent a divalent linking group, and (b) a conjugate of mutant streptavidin, comprising a molecular probe conjugated to mutant streptavidin.

2. The compound according to claim 1 or a salt thereof, which is represented by the following formula (2):

[Formula 2]

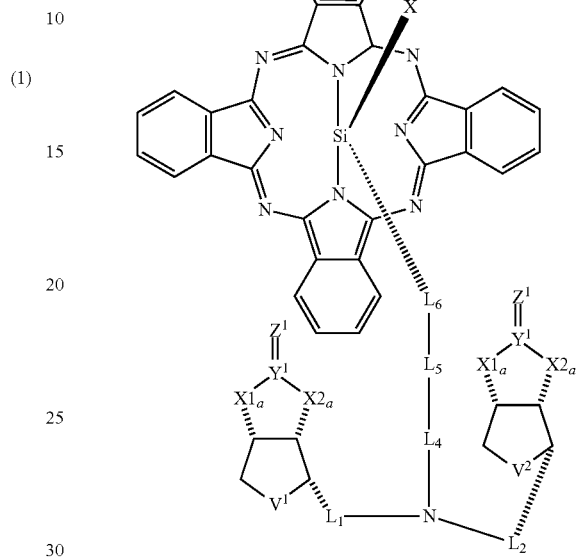

wherein each symbol is as defined in claim 1.

3. The complex according to claim 1, wherein X1a, X1b, X2a and X2b represent NH; $Y^1$ and $Y^2$ represent C; $Z^1$ and $Z^2$ represent NH; and $V^1$ and $V^2$ represent S.

4. The complex according to claim 1, wherein $L_1$ and $L_2$ each independently represent a divalent linking group consisting of a combination of groups selected from —CONH—, —NHCO—, —COO—, —OCO—, —CO—, —O—, and an alkylene group containing 1 to 10 carbon atoms.

5. The complex according to claim 1, wherein $L_4$ represents a group consisting of a combination of groups selected from —CONH—, —NHCO—, —COO—, —OCO—, —CO—, —O—, —NH—, and an alkylene group containing 1 to 10 carbon atoms.

6. The complex according to claim 1, wherein $L_5$ represents

[Formula 3]

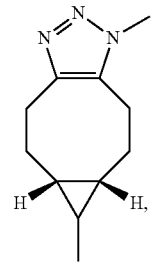

a triazole group, —S—, —CONH—, —NHCO—, —COO—, —OCO—, —CO—, —O—, —NH—, an alkylene group containing 1 to 10 carbon atoms, or a group consisting of a combination of these groups.

7. The complex according to claim 1, wherein $L_6$ represents —Si($R^1$)($R^2$)—O—, —CONH—, —NHCO—, —COO—, —OCO—, —CO—, —O—, —NH—, an alkylene group containing 1 to 10 carbon atoms, or a group consisting of a combination of these groups.

8. The complex according to claim 1, wherein the substituent having a hydrophilic group, a cationic group or an amino group at the terminus thereof, which is represented by X, is any one of the following:

[Formula 4]

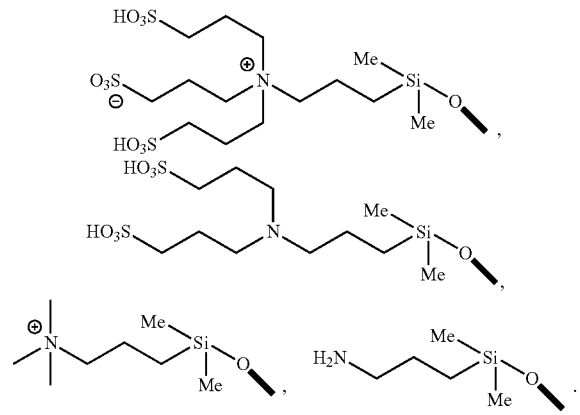

9. The complex according to claim 8, wherein the substituent having a hydrophilic group, a cationic group or an amino group at the terminus thereof, which is represented by X, is the Formula 4-3.

10. The complex according to claim 8, wherein the substituent having a hydrophilic group, a cationic group or an amino group at the terminus thereof, which is represented by X, is the Formula 4-4.

11. A therapeutic agent comprising the complex according to claim 1 and a pharmaceutically acceptable carrier.

12. A therapeutic kit comprising: (1) the complex according to claim 1, wherein the conjugate of mutant streptavidin comprises the amino acid sequence as set forth in SEQ ID NO: 1 (provided that a part of or the entire histidine tag at the C-terminus may be deleted).

13. The therapeutic kit according to claim 12, wherein the molecular probe is an anti-EREG antibody, an anti-CEA antibody, or an anti-HER2 antibody.

14. The complex according to claim 1, wherein $L_5$ is [Formula 3]

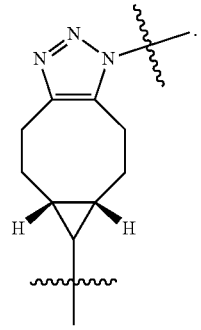 [SMILES: *C1[C@H]2CCc3c(nnn3*)CC[C@@H]12]

15. A method of suppressing proliferation of cancer cells which comprises:
    administering a complex of the complex of claim 1, and wherein the conjugate of mutant streptavidin comprises the amino acid sequence as set forth in SEQ ID NO: 1 (provided that a part of or the entire histidine tag at the C-terminus may be deleted), to a subject; and
    irradiating the cells with an excitation light in an amount effective for suppression of cell proliferation or induction of cell death.

16. The method according to claim 15, wherein the subject is affected with cancer or solid tumor.

17. The method according to claim 15, wherein wavelength of irradiation light is 660 to 740 nm.

18. The method according to claim 15, wherein light irradiation amount is 1 to 500 J/cm$^2$.

19. The method according to claim 15, wherein the molecular probe is an anti-EREG antibody, an anti-CEA antibody, or an anti-HER2 antibody.

20. A complex of claim 1, wherein the compound of (a) is any one of the following:

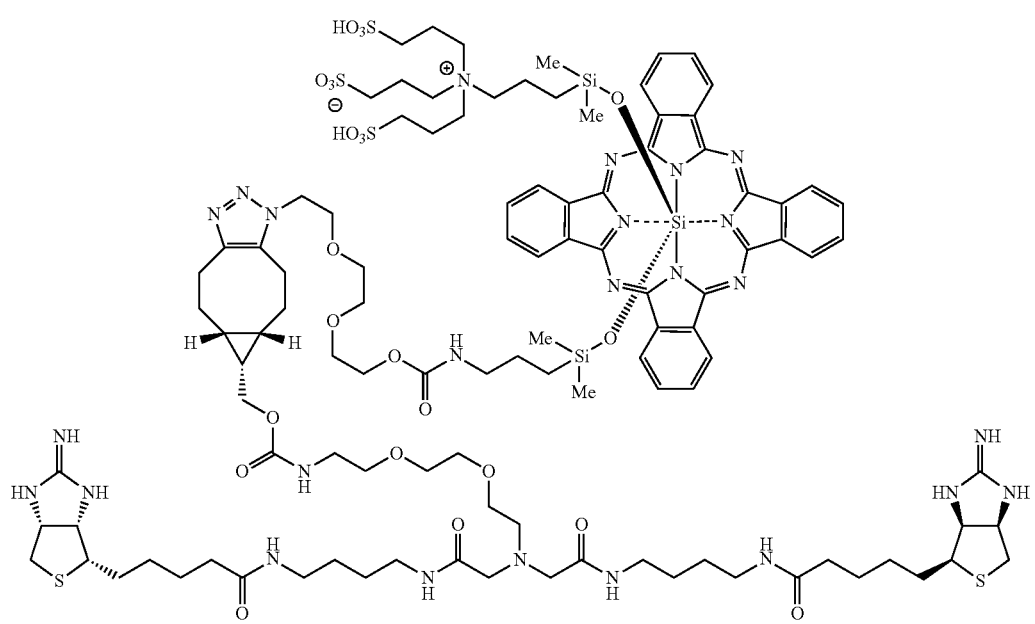

-continued
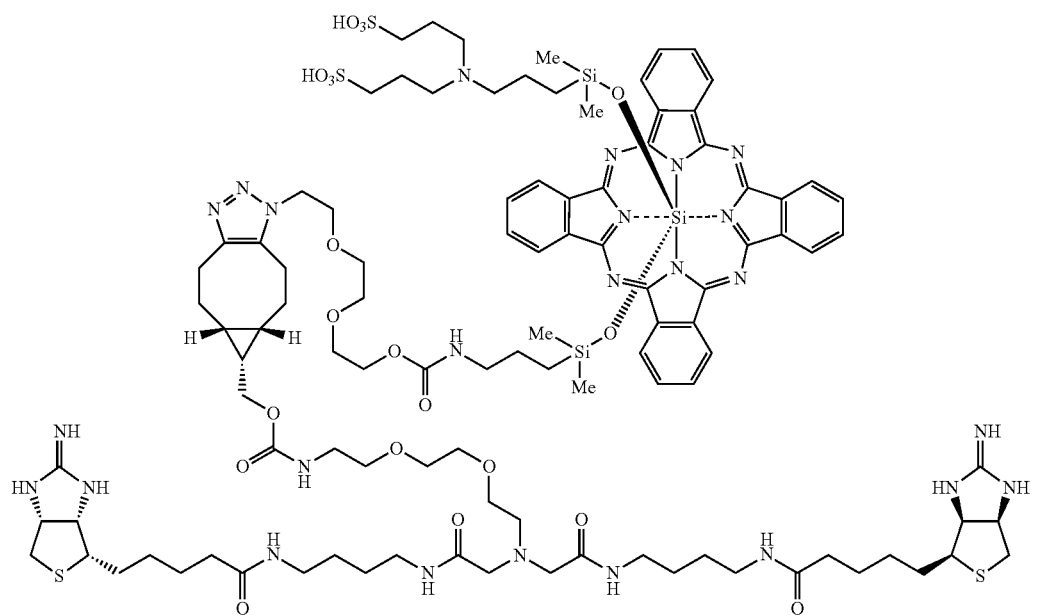
11
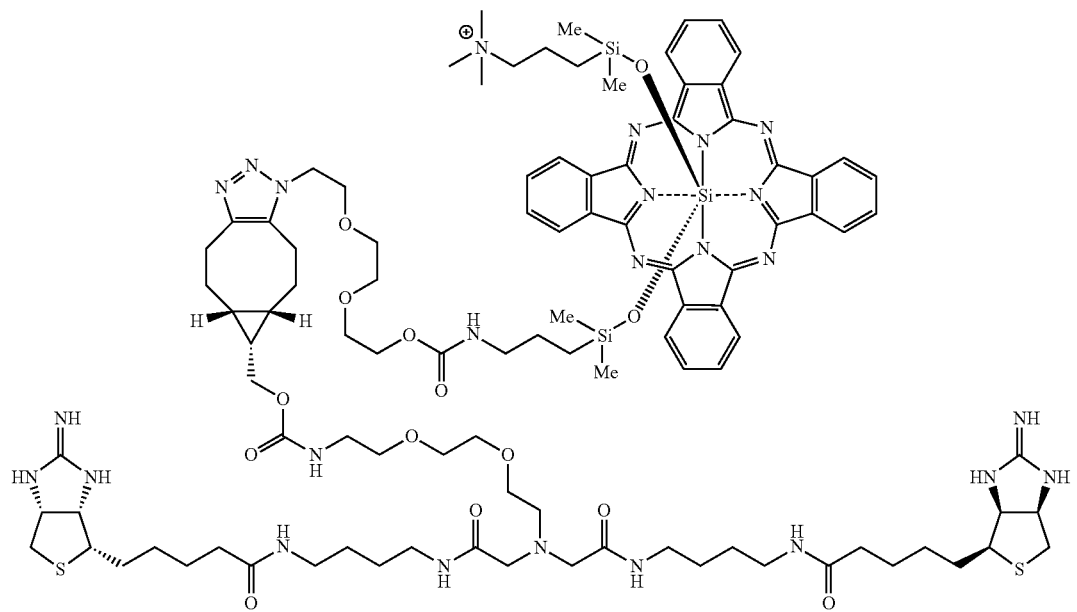
13
\* \* \* \* \*

UNITED STATES PATENT AND TRADEMARK OFFICE
CERTIFICATE OF CORRECTION

PATENT NO. : 12,115,223 B2
APPLICATION NO. : 17/237709
DATED : October 15, 2024
INVENTOR(S) : Kanai et al.

Page 1 of 1

It is certified that error appears in the above-identified patent and that said Letters Patent is hereby corrected as shown below:

In the Claims

Column 58, Line 1 (Claim 2, Line 1), please change "compound" to --complex--

Column 58, Lines 51-62 (Claim 6, Line 3), please change " 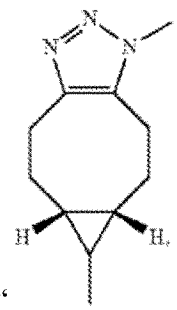 " to -- 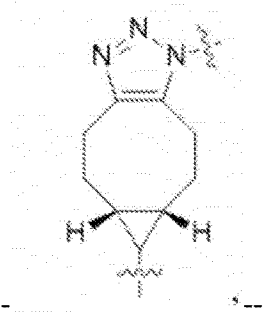 --

Column 59, Line 39 (Claim 12, Line 1), please change "comprising: (1)" to --comprising--

Signed and Sealed this
Eighteenth Day of March, 2025

Coke Morgan Stewart
*Acting Director of the United States Patent and Trademark Office*